US012790548B2

(12) United States Patent
Kandel et al.

(10) Patent No.: US 12,790,548 B2
(45) Date of Patent: Nov. 10, 2026

(54) CONTAMINANT REMOVAL DURING INTEGRATED PLASTIC RECYCLE

(71) Applicant: ExxonMobil Chemical Patents Inc., Baytown, TX (US)

(72) Inventors: Kapil Kandel, Humble, TX (US); Saurabh S. Maduskar, Houston, TX (US); Clara M. Buchanan, Houston, TX (US); Bryan A. Patel, Jersey City, NJ (US); Derrick B. Callander, Humble, TX (US); Steven M. Slack, Humble, TX (US); David H. Hopkins, Escondido, CA (US); Mei C. Soo, Cypress, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 197 days.

(21) Appl. No.: 18/730,900

(22) PCT Filed: Jan. 6, 2023

(86) PCT No.: PCT/US2023/060191
§ 371 (c)(1),
(2) Date: Jul. 22, 2024

(87) PCT Pub. No.: WO2023/141368
PCT Pub. Date: Jul. 27, 2023

(65) Prior Publication Data

US 2025/0230365 A1 Jul. 17, 2025

Related U.S. Application Data

(60) Provisional application No. 63/301,079, filed on Jan. 20, 2022.

(51) Int. Cl.
*C10G 1/02* (2006.01)
*B01D 53/02* (2006.01)
(Continued)

(52) U.S. Cl.
CPC ............... *C10G 1/02* (2013.01); *B01D 53/02* (2013.01); *B01D 53/1418* (2013.01); *C07C 4/04* (2013.01);
(Continued)

(58) Field of Classification Search
CPC . C10G 1/02; C10G 1/10; B01D 53/02; B01D 53/1418; C07C 4/04; C08J 11/12; C10B 49/22; C10B 53/07; C10B 57/14
See application file for complete search history.

(56) References Cited

U.S. PATENT DOCUMENTS 5,326,919 A 7/1994 Paisley et al. ................ 585/241
6,861,568 B1 3/2005 Guffey et al. ................ 585/241
(Continued)

FOREIGN PATENT DOCUMENTS

CN 102517062 A 6/2012
WO WO2020/252228 12/2020 ............ C10B 53/07
(Continued)

OTHER PUBLICATIONS

Chinese Office Action for CN Patent Application No. 202380017871.1 dated Jun. 12, 2026. English Translation with Original Untranslated Version, PDF file. 21 pages.

*Primary Examiner* — Ellen M McAvoy
(74) *Attorney, Agent, or Firm* — C. Tumey Law Group PLLC

(57) ABSTRACT

Systems and methods are provided for conversion of polymers (such as plastic waste) to olefins and/or feedstocks that can be further processed for formation of olefins, fuels, and/or other products. The systems and methods can include an optional thermal dehalogenation stage followed by an initial pyrolysis stage where a plastic feedstock is at least partially converted to lower boiling products. Prior to, during, and/or after the pyrolysis stage, one or more con-
(Continued)

taminant removal stages can be used in order to reduce the content of halides and/or other contaminants in the pyrolysis effluent. This can allow at least a portion of the pyrolysis effluent, such as a gas phase portion and/or a liquid phase portion of the pyrolysis effluent, to have a sufficiently low contaminant content to be used as part of a feed to a conventional petrochemical process.

22 Claims, 5 Drawing Sheets

(51) Int. Cl.

| | |
|---|---|
| ***B01D 53/14*** | (2006.01) |
| ***C07C 4/04*** | (2006.01) |
| ***C08J 11/12*** | (2006.01) |
| ***C10B 49/22*** | (2006.01) |
| ***C10B 53/07*** | (2006.01) |
| ***C10B 57/14*** | (2006.01) |

(52) U.S. Cl.
CPC ............... *C08J 11/12* (2013.01); *C10B 49/22* (2013.01); *C10B 53/07* (2013.01); *C10B 57/14* (2013.01); *B01D 2256/24* (2013.01); *B01D 2257/20* (2013.01); *C08J 2300/30* (2013.01); *C10G 2300/1003* (2013.01); *C10G 2400/20* (2013.01)

(56) References Cited

U.S. PATENT DOCUMENTS

| | | | | |
|---|---|---|---|---|
| 9,212,318 | B2 | 12/2015 | Narayanaswamy et al. | C10G 1/10 |
| 9,815,913 | B2 | 11/2017 | Costin et al. | C08F 2/04 |
| 10,513,661 | B2 | 12/2019 | Narayanaswamy et al. | C10G 1/10 |
| 12,590,252 | B2 * | 3/2026 | Wu | C10G 1/10 |
| 12,590,257 | B2 * | 3/2026 | Trapp | C10J 3/463 |
| 2016/0264880 | A1 | 9/2016 | Narayanaswamy et al. | C10G 45/08 |
| 2019/0161683 | A1 | 5/2019 | Narayanaswamy et al. | C10G 1/10 |
| 2019/0299491 | A1 * | 10/2019 | Stanislaus | B01J 29/85 |
| 2022/0195309 | A1 | 6/2022 | Uppili et al. | C10G 1/10 |
| 2022/0396735 | A1 * | 12/2022 | Wu | C10G 1/02 |
| 2023/0139587 | A1 * | 5/2023 | DeBruin | C08J 11/12 252/373 |
| 2023/0212367 | A1 * | 7/2023 | DeBruin | C08J 11/06 521/47 |
| 2024/0409822 | A1 * | 12/2024 | Hieber | C10G 1/002 |
| 2025/0059447 | A1 * | 2/2025 | Scavello | B01J 23/28 |

FOREIGN PATENT DOCUMENTS

| | | | |
|---|---|---|---|
| WO | 2021216284 A1 | 10/2021 | |
| WO | WO2021/204818 | 10/2021 | C10G 1/10 |
| WO | WO2021/211525 | 10/2021 | C10J 3/66 |

* cited by examiner

CONTAMINANT REMOVAL DURING INTEGRATED PLASTIC RECYCLE

CROSS-REFERENCE TO RELATED APPLICATIONS

This application claims the benefit of and priority to U.S. Provisional Application No. 63/301,079 filed Jan. 20, 2022, the disclosure of which is incorporated herein by reference.

FIELD

Systems and methods are provided for contaminant removal during processing of plastic waste in a pyrolysis-based processing system, such as removal of chlorine-containing and/or halogen-containing compounds. The contaminant removal can allow the resulting processed effluent to be used as an input feed for further processing, up to and/or including subsequent polymer formation using olefins produced during pyrolysis and/or during the further processing.

BACKGROUND

Recycling of plastic waste is a subject of increasing interest. Polyolefins in plastic waste are frequently converted by various methods, such as pyrolysis or gasification, to produce energy. To modify the process, so that the polymers can be instead recycled for return to the same or similar original usage, these pyrolysis and gasification products need to go through further pyrolysis or conversion processes to return them back to the light olefin monomer. The olefin monomers can then be repolymerized back to the original polyolefin for use in the same or similar service. Unfortunately, the process to make light olefins is high in energy usage, capital required, and produces relatively low yields of the light olefin monomers. It would be desirable to develop systems and methods that can allow for a recycle path for polyolefins with improved olefins yields.

U.S. Pat. No. 5,326,919 describes methods for monomer recovery from polymeric materials. The polymer is pyrolyzed by heating the polymer at a rate of 500° C./second in a flow-through reactor in the presence of a heat transfer material, such as sand. Cyclone separators are used for separation of fluid products from solids generated during the pyrolysis. However, the resulting vapor phase monomer product corresponds to a mixture of olefins, and therefore is not suitable for synthesis of new polymers.

U.S. Pat. No. 9,212,318 describes a catalyst system for pyrolysis of plastics to form olefins and aromatics. The catalyst system includes a combination of an FCC catalyst and a ZSM-5 catalyst.

U.S. Pat. No. 10,513,661 describes an integrated process for converting plastic waste that includes pyrolysis of plastic waste to form an effluent, hydroprocessing a liquid portion of the effluent to form a treated effluent, and then performing steam cracking on a portion of the treated effluent. The hydroprocessing of the liquid portion of the effluent to form the treated effluent is described as a hydrocracking process that acts in part to further reduce the chlorine content.

U.S. Pat. No. 6,861,568 describes a method for performing radical-initiated pyrolysis on plastic waste dissolved in an oil medium. After mixing the plastic waste with oil, the mixture is delivered to a pyrolysis vessel. The pyrolysis temperature is generally described as 300° C.-375° C., although an example is provided of partial reaction at 275° C. Based on the pyrolysis conditions, one of the two primary products is a reactor overhead stream that includes a desired distillate product and a non-condensible overhead gas product. After condensing out the desired distillate product, the remaining overhead gas product can be treated with a water wash in an effort to remove any HCl that may be present. Thus, HCl removal is accomplished using a separate, additional water wash stage.

U.S. Pat. Nos. 7,146,130 and 9,815,913 describe polymerization processes.

SUMMARY

In various aspects, a method for performing chemical recycling of plastic waste is provided. The method can include thermally dehalogenating a plastic feedstock to form a thermally dehalogenated feedstock and dehalogenation product. The thermal dehalogenation can correspond to, for example, thermal dechlorination. Optionally, a basic compound (such as a calcium-containing compound) can be included in the thermal dechlorination environment. The method can further include pyrolyzing at least a portion of the thermally dehalogenated feedstock in a pyrolysis reactor at a temperature of 400° C. or more to form a pyrolysis effluent. The pyrolysis environment can correspond to, for example, a fluidized bed of heat transfer particles. The method can further include separating the pyrolysis effluent to form a pyrolysis gas fraction and a pyrolysis liquid fraction. The method can further include converting at least a portion of the pyrolysis liquid fraction to form a conversion effluent comprising 10 wppm or more of one or more halide components. The method can further include washing at least a portion of the conversion effluent to remove at least a portion of the one or more halide components from a washed conversion effluent. Additionally, the method can include separating at least a portion of the washed conversion effluent to form a) an ethylene product stream comprising 99.0 vol % ethylene and 1.0 wppm or less of the one or more halide compounds, b) a propylene product stream comprising 99.0 vol % propylene and 1.0 wppm or less of the one or more halide compounds, or c) a combination of a) and b).

DETAILED DESCRIPTION

Figure 1:
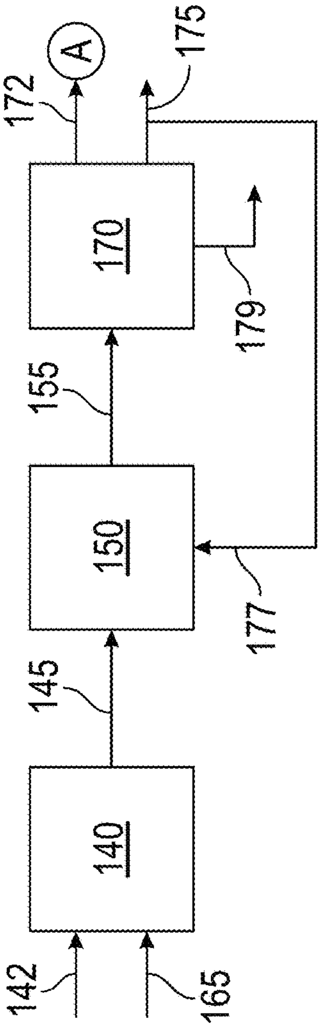
FIG. 1 shows an example of a portion of an integrated process train for pyrolysis and processing of a plastic feedstock.

All numerical values within the detailed description and the claims herein are modified by "about" or "approximately" the indicated value, and take into account experimental error and variations that would be expected by a person having ordinary skill in the art.

In various aspects, systems and methods are provided for conversion of polymers (such as plastic waste) to olefins and/or feedstocks that can be further processed for formation of olefins, fuels, and/or other products. The systems and methods can include an optional thermal dehalogenation stage followed by an initial pyrolysis stage where a plastic feedstock is at least partially converted to lower boiling products. Prior to, during, and/or after the pyrolysis stage, one or more contaminant removal stages can be used in order to reduce the content of halides and/or other contaminants in the pyrolysis effluent. This can allow at least a portion of the pyrolysis effluent, such as a gas phase portion and/or a liquid phase portion of the pyrolysis effluent, to have a sufficiently low contaminant content to be used as part of a feed to a conventional petrochemical process. Examples of such processes can include steam cracking or another feed conversion process for creating olefinic components from the at least a portion of the pyrolysis effluent. Thus, by performing sufficient contaminant removal, existing types of petrochemical processes (such as steam cracking) can be incorporated into a process flow for chemical recycling. Optionally, additional contaminant removal can be performed after processing in at least one petrochemical process. This can reduce or minimize the halide content in the olefinic components (such as ethylene or propylene) so that the olefinic components can be suitable for use as a feed to a commercial-scale polymerization process.

Chemical recycling provides a pathway for breaking down plastic molecules into fundamental building blocks so that this material can be recycled to form new plastic products, the new products optionally corresponding to products that are substantially similar to and/or the equivalent of the original material. High temperature thermal pyrolysis is one type of chemical recycling that can provide an efficient and robust method of pyrolyzing plastic waste.

Unfortunately, in addition to the polymers that are desired for chemical recycle, plastic waste can also contain a variety of heteroatoms (i.e., non-carbon and non-hydrogen atoms). Heteroatoms can be introduced to plastic waste in several ways including, but not limited to, incorporation of dyes, antioxidants, or other additives into a plastic when it is formulated, and/or exposure to dirt and other waste materials in the waste collection process. Additionally, some heteroatoms can be integral to the formation of certain types of polymers, such as nitrogen present in polyamides (e.g., nylon) and polynitriles; chlorine in polyvinylchloride; and/or oxygen in ethylene-vinyl acetate or polyethylene terephthalate.

During chemical recycling of plastic waste, the non-carbon, non-hydrogen heteroatoms are essentially contaminants that can be detrimental to conventional petrochemical processes in a variety of ways. One group of heteroatom contaminants that can pose particular challenges for plastic waste recycling are halide contaminants. Some halogen contaminants, such as fluorine and chlorine, are integral to the formation of certain types of polymers, and therefore can be present in plastic waste in substantial quantities. Examples of such polymers include polyvinylchloride (PVC), polyvinylidene chloride (PVDC), polytetrafluoroethylene (PTFE), and polyvinylidene fluoride (PVDF). Other halogen contaminants, such as bromine or iodine, can be present in various types of specialty polymers. For example, some types of brominated polymers are used as flame retardants. Such flame retardant polymers can be blended with other polymers, such as polystyrene foam. In addition to direct inclusion as part of a polymer, halogens can also be present in various additives that are used to modify the properties of formulated polymers.

Halide contaminants present in plastic waste can pose a variety of challenges. For example, the presence of halogens within a processing environment can often cause degradation of the structural materials used to define the processing environment. This can result in reduced run lengths due to increased maintenance requirements and/or due to fouling of equipment. Other issues can be related to downstream uses for products derived from plastic waste. As an example, some polymerization catalysts can have high sensitivity to the presence of halogens in the polymerization environment.

Another group of issues can be related to where contaminants can end up when separating a process effluent to form commercial products. For example, in many types of process trains for handling pyrolysis effluents, any chlorine compounds present in the pyrolysis effluent have the potential to eventually be concentrated (in the form of $CH_3Cl$) in a propane product that is formed as part of separating olefins from the effluent and can cause corrosion issues. As another example, after forming a pyrolysis effluent, various portions of a pyrolysis effluent can be exposed to hydroprocessing catalysts, such as hydrogenation catalysts. Any halogen compounds present in a hydroprocessing environment can potentially degrade the activity of hydroprocessing catalysts.

Still other types of contaminants can also cause difficulties when present in plastic waste. Metalloids and/or metals such as silicon and mercury can be damaging for catalysts that may be used in some types of processing stages. Additionally, other types of heteroatoms, such as sulfur, nitrogen, and oxygen, can be heteroatoms that are generally encountered in petrochemical processing, but that may not be readily handled in the specific conventional petrochemical processes that would be desirable for incorporation into a chemical recycling process train.

One option for handling heteroatom, metal, and/or metalloid contaminants in plastic waste could be to use hydroprocessing to remove at least a portion of the contaminants. Unfortunately, there are several difficulties with incorporating hydroprocessing as part of a contaminant removal process. First, although hydroprocessing can assist with removing contaminants such as chlorine, silicon, and/or mercury from a feed based on plastic waste, a hydroprocessing stage accomplishes this removal at the expense of degrading the hydroprocessing stage. For example, under the conditions typically present in a hydroprocessing environment, the presence of chlorine and/or other halogens can result in corrosion of a variety of exposed surfaces. This can potentially sharply reduce run times for a hydroprocessing unit. It would be desirable if at least the chlorine removal and/or halogen removal could be accomplished in processing stages with vessels that have reduced complexity. Additionally or alternately, it would be beneficial to accomplish chlorine removal and/or halogen removal in processing stages that are less costly to have in parallel (so that the overall chemical recycling system can continue to operate during routine maintenance) and/or in processing stages that are more easily constructed from corrosion-resistant materials.

As another example, contaminants such as silicon and mercury can act as catalyst poisons for the types of catalysts used in hydroprocessing. It is possible to use guard beds of lower cost catalyst in a hydroprocessing stage, but this can still require either higher frequency shut down of the hydroprocessing stage for maintenance and/or a size expansion for a relatively high cost processing stage. Thus, it would be beneficial to be able to remove silicon and/or mercury prior to exposing a potential feed to a hydroprocessing catalyst.

The elevated cost of operation of a hydroprocessing stage also poses challenges for use in contaminant removal. In many conventional refinery or petrochemical processing settings, hydrogen is a relatively high cost resource. The goal of an initial group of processing stages is to be able to convert plastic waste into a feed that can then be processed in conventional petrochemical processes. If hydroprocessing is used in the initial group of processing stages, this can sharply increase the cost of performing the initial plastic waste processing.

In various aspects, systems and methods are provided for performing pyrolysis on plastic waste as part of an initial group of processing stages for use in an integrated chemical recycling process. In addition to at least one pyrolysis stage, the initial group of processing stages can include one or more types of contaminant removal stages. This can optionally include a thermal dehalogenation stage prior to the initial pyrolysis stage. The various processing stages in the initial group of processing stages can be used to reduce or minimize various types of contaminants, so that downstream (conventional) petrochemical processing stages can be used as part of the integrated chemical recycling process with a reduced or minimized amount of modification. Additionally, the initial group of processing stages can perform the contaminant removal while reducing or minimizing exposure of the contaminants to hydroprocessing stages and/or other processing stages that have elevated capital and/or operational costs. This can facilitate integration of processing of a gas phase portion of the pyrolysis effluent and/or a liquid phase portion of the pyrolysis effluent with conventional petrochemical processing stages.

A variety of contaminants from plastic waste could potentially need to be removed in order to protect conventional petrochemical operations. These contaminants include but are not limited to oxygenates, halides, metals, nitrogen-containing contaminants, sulfur-containing contaminants, and phosphorus-containing contaminants. For example, the contaminants can include, carbon monoxide, carbon dioxide, methyl chloride, ethyl chloride, vinyl chloride, chloroaromatics, nitrogen oxides (NOx), silicon, sulfur oxides (SOx), organic halides, arsenic, and phosphorus. Several contaminant removal operations could be employed to remove these contaminants. These removal operations could be performed either in the pre-treatment step and/or on the vapor and/or liquid product streams. These contaminant removal steps include but are not limited to water wash, fixed bed adsorption, liquid extraction, caustic wash, amine wash, calcium oxide adsorption, or contacting with other specialized adsorption material. Optionally, some types of products can also be recycled to a pyrolysis stage (such as a steam cracking stage) to allow for further contaminant removal, such as further conversion of organic halides to inorganic halides which can be removed, for example, by downstream water wash processes.

The contaminant removal stages can be incorporated into an integrated chemical recycling configuration in one or more locations. Potential locations in the process flow for contaminant removal can include, but are not limited to, removal of contaminants prior to the initial pyrolysis of the feed; contaminant removal as part of the pyrolysis process; removal of contaminants from a liquid recycle portion of the pyrolysis effluent; removal of contaminants from a gas phase portion of the pyrolysis effluent; and/or removal of contaminants from a liquid product portion of the pyrolysis effluent.

In this discussion, a liquid product/liquid phase portion is defined as a product/portion that is in the liquid state at 25° C. and 100 kPa-a. A gas or vapor product/gas or vapor portion is defined as a product/portion that is in the gas phase at 25° C. and 100 kPa-a. It is noted that at some points during processing, a liquid product/portion may be present in a gaseous phase due to an increased temperature (and/or the combination of temperature and pressure) within the reaction system. Similarly, depending on the nature of the full configuration used, a vapor product/portion may be in a liquid phase due to the combination of temperature and pressure at a location within the reaction system.

In this discussion, a reference to a "$C_x$" fraction, stream, portion, feed, or other quantity is defined as a fraction (or other quantity) where 50 wt % or more of the fraction corresponds to hydrocarbons having "x" number of carbons. When a range is specified, such as "$C_x$-$C_y$", 50 wt % or more of the fraction corresponds to hydrocarbons having a number of carbons between "x" and "y". A specification of "$C_{x+}$" (or "$C_{x-}$") corresponds to a fraction where 50 wt % or more of the fraction corresponds to hydrocarbons having the specified number of carbons or more (or the specified number of carbons or less).

Plastic Feedstock

In various aspects, a plastic feedstock for pyrolysis can include or consist essentially of one or more types of polymers, such as polymers corresponding to plastic waste. The systems and methods described herein can be suitable for processing plastic waste corresponding to a single type of olefinic polymer and/or plastic waste corresponding to a plurality of olefinic polymers. In aspects where the feedstock consists essentially of polymers, the feedstock can include one or more types of polymers as well as any additives, modifiers, packaging dyes, and/or other components typically added to a polymer during and/or after formulation. The feedstock can further include any components typically found in polymer/plastic waste.

In some aspects, the polymer feedstock can include at least one of polyethylene and polypropylene. The polyethylene can correspond to any convenient type of polyethylene, such as high density or low density versions of polyethylene. Similarly, any convenient type of polypropylene can be used. In some aspects, the polyethylene and polypropylene can be present in the mixture as a co-polymer of ethylene and propylene. Additionally or alternately, the plastic feedstock can include one or more of polystyrene, polyvinylchloride, polyvinylidene chloride, polyamide (e.g., nylon), polyethylene terephthalate, polytetrafluoroethylene, polyvinylidene fluoride, and ethylene vinyl acetate. Still other polyolefins can correspond to polymers (including co-polymers) of butadiene, isoprene, and isobutylene. More generally, the polyolefins can include co-polymers of various olefins, such as ethylene, propylene, butenes, hexenes, and/or any other olefins suitable for polymerization. Optionally, the plastic feedstock can include 0.01 wt % or more of one or more halogenated polymers (e.g., chlorinated polymers, brominated polymers, fluorinated polymers, iodinated polymers). For example, the plastic feedstock can optionally contain 0.01 wt % to 25 wt % of one or more halogenated polymers, or 0.1 wt % to 25 wt %, or 1.0 wt % to 25 wt %, or 2.0 wt % to 25 wt %, or 5.0 wt % to 25 wt %, or 10 wt % to 25 wt %, or 0.01 wt % to 15 wt %, or 0.1 wt % to 15 wt %, or 1.0 wt % to 15 wt %, or 2.0 wt % to 15 wt %, or 5.0 wt % to 15 wt %.

In this discussion, unless otherwise specified, weights of polymers in a feedstock correspond to weights relative to the total polymer content in the feedstock. Any additives/modifiers/other components included in a formulated polymer are included in this weight. However, the weight percentages described herein exclude any solvents or carriers that might optionally be used to facilitate transport of the polymer into the initial pyrolysis stage.

In some aspects, a plastic feedstock can primarily correspond to a single type of polymer, such as being substantially composed of a single polymer or even consisting essentially of a single polymer. In other aspects, a plastic feedstock can correspond to a mixture of polymers. For example, in some aspects the maximum content of any single type of polymers (e.g., polyethylene, polypropylene, polystyrene) in the plastic feedstock can be 80 wt % or less, or 65 wt % or less, or 50 wt % or less, or 40 wt % or less, such as down to 15 wt % or possibly still lower. Additionally or alternately, in some aspects the combined content of any two types of polymers in the plastic feedstock can be 90 wt % or less, or 80 wt % or less, or 65 wt % or less, or 50 wt % or less, such as down to 25 wt % or possibly still lower. It is noted that when considering a "type" of polymer, versions of a polymer that are substantially similar except for molecular weight are considered to be the same type of polymer. For example, for the purposes of determining polymer type, low density polyethylene and ultra-high molecular weight polyethylene are both considered to be polyethylene, and therefore are the same type of polymer. With regard to co-polymers, if the weight percentage of at least one monomer unit type varies by more than 5.0 wt % between two polymers, or if a new monomer unit is present in an amount corresponding to 1.0 wt % or more of the polymer, then the polymers are considered to be of different types. Thus, co-polymers of different molecular weight and/or different block size within the polymer but having the same ratio of monomer units are considered to be the same type of polymer. As another example, if a first co-polymer includes 55 wt % ethylene and 45 wt % polypropylene, a second co-polymer including 53 wt % ethylene, 47 wt % propylene would be considered as the same type of polymer as the first co-polymer. By contrast, a third co-polymer including 49 wt % ethylene and 51 wt % polypropylene would be considered as a different type of polymer than the first co-polymer. Similarly, a co-polymer including 53 wt % ethylene, 45 wt % propylene, and 2.0 wt % styrene would be considered a different type of polymer than the first co-polymer.

In addition to having maximum amounts of some polymer types, another option can be to have minimum amounts for some polymer types. In some aspects, at least two different types of polymers can be present within a plastic feedstock in an amount of 20 wt % or more, or 25 wt % or more, or 30 wt % or more, such as up to 45 wt % or possibly still higher. Additionally or alternately, in some aspects, at least three different types of polymers can be present within a feedstock in an amount of 15 wt % or more, or 20 wt % or more, or 25 wt % or more, such as up to 30 wt % or possibly still higher. As an example of at least two different types of polymers being present within a feedstock in an amount of 20 wt % or more, a plastic feedstock could include 20 wt % or more of polyethylene and polypropylene; or 20 wt % or more of polyethylene and polystyrene; or 20 wt % or more of polystyrene and polyvinylchloride; or any other convenient combination of polymers. In some aspects, a plastic feedstock can include at least two different types of polymers in an amount of 20 wt % or more, where one or more of the polymers present in an amount of 20 wt % or more is different from polyethylene and polypropylene. In some aspects, a plastic feedstock can include at least three different types of polymers in an amount of 15 wt % or more, where two or more of the polymers present in an amount of 15 wt % or more are different from polyethylene and polypropylene.

In some aspects, the plastic feedstock can include at least one polymer that corresponds to a polymer that includes contaminants as part of the polymer structure. For example, in some aspects the plastic feedstock can include one or more types of polymers, or two or more types of polymers, or three or more types of polymers that are polymers that include contaminants as part of the polymer structure. Examples of such polymers include, but are not limited to, chlorinated polymers (e.g., polyvinyl chloride, polyvinylidene chloride); brominated polymers (e.g., polybrominated diphenyl ethers, hexabromocyclododecane, and/or brominated styrene); fluorinated (e.g., polymers polyvinylidene fluoride, polytetrafluorethylene); nitrogen-containing polymers (e.g., nylon, other polyamides, polynitriles); and/or oxygen-containing polymers (e.g., polyethylene terephthalate, polyethers, polyesters).

In some aspects, the plastic feedstock can include 0.01 wt % to 100 wt % of polyethylene, polypropylene, or a combination thereof, or 0.01 wt % to 80 wt %, or 0.01 wt % to 49 wt %, or 0.01 wt % to 25 wt %, or 1.0 wt % to 100 wt %, or 1.0 wt % to 80 wt %, or 1.0 wt % to 49 wt %, or 1.0 wt % to 25 wt %, or 10 wt % to 100 wt %, or 10 wt % to 80 wt %, or 10 wt % to 49 wt %, or 30 wt % to 100 wt % or 30 wt % to 80 wt %.

Another potential feed component can be a polymer that includes chlorine. In some aspects, the plastic feedstock can include 0.01 wt % to 25 wt %, or 0.1 wt % to 25 wt %, or 1.0 wt % to 25 wt %, or 11 wt % to 25 wt %, or 0.01 wt % to 10 wt %, or 0.1 wt % to 10 wt %, or 0.01 wt % to 2.0 wt %, or 0.01 wt % to 1.0 wt % of polyvinyl chloride, polyvinylidene chloride, or a combination thereof. Polyvinyl chloride is roughly 56% chlorine by weight, while polyvinylidene dichloride includes still greater amounts of chlorine by weight. As a result, pyrolysis of polyvinyl chloride (and/or polyvinylidene chloride) can result in formation of substantial amounts of hydrochloric acid relative to the initial weight of the polyvinyl chloride and/or polyvinylidene chloride.

Yet another potential feed component can be a polymer that includes bromine, such as polybrominated diphenyl ethers, hexabromocyclododecane, and/or brominated styrene. In some aspects, the plastic feedstock can include 0.01 wt % to 25 wt %, or 0.1 wt % to 25 wt %, or 1.0 wt % to 25 wt %, or 11 wt % to 25 wt %, or 0.01 wt % to 10 wt %, or 0.1 wt % to 10 wt %, or 0.01 wt % to 2.0 wt %, or 0.01 wt % to 1.0 wt % of one or more bromine-containing polymers. Pyrolysis of bromine-containing polymers can result in formation of hydrobromic acid.

Additionally or alternately, in some aspects, the plastic feedstock can include 0.01 wt % to 1.0 wt %, or 0.1 wt % to 1.0 wt %, of polytetrafluoroethylene (PTFE), polyvinylidene fluoride (PVDF), or a combination thereof. PVDF is roughly 60% fluorine by weight, while PTFE includes still greater amounts of fluorine by weight. As a result, pyrolysis of PVDF (and/or PTFE) can result in formation of substantial amounts of hydrofluoric acid relative to the initial weight of the PVDF and/or PTFE.

In some aspects the plastic feedstock can optionally include 0.01 wt % to 35 wt % of polystyrene, or 0.1 wt % to 35 wt %, or 1.0 wt % to 35 wt %, or 0.01 wt % to 20 wt %, or 0.1 wt % to 20 wt %, or 1.0 wt % to 20 wt %, or 10 wt % to 35 wt %, or 5 wt % to 20 wt %. In some aspects the plastic feedstock can optionally include 0.01 wt % to 35 wt % of polynitrile (e.g., polyacrylonitrile), or 0.1 wt % to 35 wt %, or 1.0 wt % to 35 wt %, or 0.01 wt % to 20 wt %, or 0.1 wt % to 20 wt %, or 1.0 wt % to 20 wt %, or 10 wt % to 35 wt %, or 5 wt % to 20 wt %. In some aspects the plastic feedstock can optionally include 0.01 wt % to 35 wt % of polyethylene terephthalate, or 0.1 wt % to 35 wt %, or 1.0 wt % to 35 wt %, or 0.01 wt % to 20 wt %, or 0.1 wt % to 20 wt %, or 1.0 wt % to 20 wt %, or 10 wt % to 35 wt %, or 5 wt % to 20 wt %. In some aspects the plastic feedstock can optionally include 0.01 wt % to 35 wt % of ethylene-vinyl acetate, or 0.1 wt % to 35 wt %, or 1.0 wt % to 35 wt %, or 0.01 wt % to 20 wt %, or 0.1 wt % to 20 wt %, or 1.0 wt % to 20 wt %, or 10 wt % to 35 wt %, or 5 wt % to 20 wt %. In some aspects the plastic feedstock can optionally include 0.01 wt % to 35 wt % of polyamide, or 0.1 wt % to 35 wt %, or 1.0 wt % to 35 wt %, or 0.01 wt % to 20 wt %, or 0.1 wt % to 20 wt %, or 1.0 wt % to 20 wt %, or 10 wt % to 35 wt %, or 5 wt % to 20 wt %.

In various aspects, the plastic waste can be prepared for use as a pyrolysis feedstock. In some aspects, this can include using one or more physical processes to convert the plastic feedstock into particles and/or to reduce the particle size of the plastic particles. Processing a plastic feedstock to have particles of a target size can facilitate introducing the plastic feedstock into the pyrolysis stage in several ways. One option can be to directly introduce the particles into the pyrolysis reactor, such as by using a screw feeder. Another option can be to form a slurry or a solution of plastic by adding a co-feed to the particles, and then introducing the slurry or solution into the pyrolysis reactor.

For plastic waste feedstock that is not initially in the form of particles, a first processing step can be a step to convert the plastic feedstock into particles. This can be accomplished using any convenient method. In some aspects, this can correspond to physical processing, such as chopping, crushing, grinding, shredding or another type of physical conversion of plastic solids into particles and/or physical processing to reduce particle size. Additionally or alternately, this can correspond to melting of plastic followed by a convenient method for forming particles from molten plastic. For example, liquid phase plastic can be extruded through a die to form plastic particles of a desired size and/or shape. Optionally, melting followed by particle formation can be used even if the plastic is already in a particulate form. It is noted that it may be desirable to convert plastic into particles of a first average and/or median size, followed by additional physical processing to reduce the size of the particles.

Having a small particle size can facilitate transport of the solids into the pyrolysis reactor. Smaller particle size can potentially also contribute to achieving a desired level of conversion of the polymers/polyolefins under the short residence time conditions of the pyrolysis. Thus, physical processing can optionally be performed to reduce the median particle size of the plastic particles to 3.0 cm or less, or 2.5 cm or less, or 2.0 cm or less, or 1.0 cm or less, such as down to 0.01 cm or possibly still smaller. For determining a median particle size, the particle size is defined as the diameter of the smallest bounding sphere that contains the particle. Alternatively, in aspects where plastic is melted and particles are formed (such as by extrusion), the particles can be formed to have the desired median particle size.

Still another option for introducing plastic into the pyrolysis stage can be to melt the plastic to form a fluid flow of the plastic. An extruder, for example, can then be used to introduce the melted plastic into the pyrolysis reactor. Optionally, a co-feed could be introduced along with such melted plastic.

Optionally, a portion of the feed can correspond to a recycled portion of the liquid effluent. This can correspond to a portion of the entire liquid effluent, at least a portion of one or more higher boiling fractions of the liquid effluent, or at least a portion of a bottoms portion of the liquid effluent. Recycle of a portion of the entire liquid effluent can simplify the recycle loop, but can lead to some loss of yield as lower boiling liquid products are converted to gas products. Recycle of a bottoms portion can be beneficial for reducing or minimizing the amount high boiling components in the resulting liquid product, such as 566° C.+ products, or 538° C.+ products, or 510° C.+ products. This can be beneficial, for example, if the resulting liquid product (i.e., the portion not used for recycle) is subsequently used as an input for a steam cracking process. Additionally or alternately, if a sufficient amount of liquid product recycle is used, the recycle may be sufficient to allow the plastic feed to be dissolved in the recycle stream, which can simplify introduction of the plastic waste into the pyrolysis stage.

In some aspects, substantially all of the feed into the initial pyrolysis stage can correspond to plastic waste, with some portions of the feed optionally corresponding to recycled portions of the liquid effluent. In other aspects, another option can be to use an additional feedstock as a co-feed. Such a co-feed can be used in addition to and/or in place of having a recycle stream. An additional feedstock can correspond to a conventional mineral feed, a bio-derived feed, or any other feed that can be processed via pyrolysis. One example for a use of an additional feedstock can be in aspects where a recycle stream is used to dissolve the plastic waste. Using an additional feedstock can potentially reduce the amount of recycle. Additionally or alternately, during startup of a process flow that includes recycle, an additional feedstock can be used to supplement the recycle stream until a sufficient amount of plastic waste has been processed to provide the desired volume of recycle.

In aspects where a solution is formed by combining the plastic feedstock with a recycle stream and/or one or more additional feedstocks, the amount of plastic feedstock in the resulting combined feed can correspond to 1.0 wt % to 80 wt % of the combined feed, or 1.0 wt % to 50 wt %.

Contaminant Removal Stage—Prior to Initial Pyrolysis (e.g., Thermal Dehalogenation)

One location for a contaminant removal stage is prior to exposing the feedstock to the initial pyrolysis stage. Such contaminant removal can occur during physical processing of the feedstock to achieve a desired particle size and/or state for the feedstock, or after physical processing.

In some aspects, at least a portion of a contaminant removal stage prior to pyrolysis can correspond to physical contaminant separation processes. For example, prior to incorporation into a feedstock, plastic waste may be mixed with a variety of other types of waste. Rinsing or washing of the plastic waste, optionally prior to and/or after formation of plastic particles of a target size, can assist with removing other types of waste residues that may be adhered to the surface of the plastic.

Another type of contaminant removal that can be performed prior to pyrolysis is chlorine removal, such as chlorine removal by thermal dechlorination. More generally, the contaminant removal can correspond to halogen removal, such as halogen removal by thermal dehalogenation. In some aspects where a solution of plastic feedstock is formed (using a liquid recycle stream and/or a co-feed), the solution can be heated in a vessel to a temperature between 170° C. to 350° C., or 170° C. to 300° C., or 170° C. to 250° C., while optionally passing a purge gas through the solution. Heating in a vessel to a temperature of 170° C. to 350° C. (or 170° C. to 300° C.) for a period of time (such as 1.0 minutes to 240 minutes) can allow for decomposition of chlorine-containing functional groups, bromine-containing functional groups, and/or iodine-containing functional groups in polymers in the plastic feedstock while reducing or minimizing other types of conversion of the polymer backbones, the recycle stream, and/or any additional feedstocks. In some aspects, decomposition of some fluorine-containing groups can also occur. The chlorine products (e.g., HCl) and/or other halogen products (e.g., HF, HBr, HI) generated by this heating can then be carried away from the vessel by a purge gas. By performing the dehalogenation at a temperature of 250° C. or less (or optionally 300° C. or less), the dehalogenation can be accomplished while reducing or minimizing the amount of volatile organic compounds (such as light ends or low boiling naphtha compounds) that are formed during the dehalogenation process. By substantially avoiding the formation of low boiling compounds other than hydrogen halides (i.e., HCl, HBr, HI, HF), the HCl and/or other hydrogen halides can be removed from the dehalogenation environment while reducing or minimizing incorporation of carbon-containing compounds into the purge exhaust stream from the dehalogenation environment. This can avoid the need to process the purge exhaust stream, which contains HCl and/or hydrogen halides, in order to recover desirable carbon-containing products. Additionally, performing the dehalogenation in the mixing vessel means that the chlorides are removed prior to co-processing, thus reducing or minimizing the potential for corrosion of downstream equipment.

It is noted that in some aspects, using a dehalogenation temperature of greater than 250° C. can reduce or minimize one of the benefits performing the dehalogenation prior to co-processing. In particular, one of the difficulties with performing dehalogenation at higher temperatures is that the resulting chlorine species and/or halogen species that are evolved (such as HCl) are mixed with other carbon-containing products. While HCl and/or other hydrogen halides can be separated from products in the purge gas exhaust, needing to separate desired carbon-containing products from HCl means that an increased number of components in the reaction system will be exposed to the potentially corrosive effects of the HCl. Performing the dehalogenation in a vessel prior to co-processing can reduce or minimize this difficulty by reducing or minimizing the amount of carbon-containing products that might be entrained with the HCl and/or other hydrogen halides in the purge gas exhaust. Using a dehalogenation temperature of 250° C. or less assists with this valuable feature, as using a low dehalogenation temperature can reduce or minimize the amount of decomposition of the one or more additional feedstocks during dehalogenation.

When performing a thermal dehalogenation process, another option can be to also include a source of calcium and/or another source of metal/material with basic properties in the thermal dechlorination environment. For example, various types of calcium additives can be included in a thermal dechlorination environment, including (but not limited to) $Ca(OH)_2$, CaO, and/or $CaCO_3$. During thermal dehalogenation of a plastic feedstock, chlorine that evolves from thermal decomposition of a polymer can typical evolve in the form of HCl. The presence of a calcium additive can be beneficial during thermal dehalogenation by allowing at least a portion of the HCl to be converted into $CaCl_2$. The stoichiometry of the additional product(s) formed can depend on the nature of the calcium additive. $CaCl_2$ formed in the thermal dehalogenation environment is a solid that has a relatively low solubility in heavy crude oil fractions. By forming $CaCl_2$, potentially highly corrosive HCl can be converted into a solid compound with low or minimal potential for causing corrosion of surfaces in the reaction environment. The $CaCl_2$ formed in a thermal dehalogenation environment can be removed by any convenient method, such as settling, centrifugation, and/or filtration. It is noted that some sodium compounds, such as $NaCO_3$, can also be used as reagent additives in a thermal dehalogenation environment to facilitate removal of resulting chlorine-containing compounds from the reaction environment. More generally, various types of metals/materials with basic properties that allow for formation of a solid halide compound can be used to facilitate removal of halogens that are evolved as hydrogen halides in the thermal dehalogenation environment.

It is noted that including a calcium additive and/or other basic additive in the thermal dehalogenation environment can reduce or minimize the need for using a purge gas in the thermal dehalogenation environment. For example, while both a purge gas and a calcium additive can be used, the addition of a calcium additive results in substantial conversion of HCl formed during thermal dehalogenation into a solid dehalogenation product. Such a solid dehalogenation product can be filtered or otherwise physically separated from the remainder of the feedstock. The gas phase products formed in place of HCl can correspond to compounds such as $CO_2$ and/or $H_2O$. While $CO_2$ and/or $H_2O$ can be removed from the environment using a purge gas, there are a variety of other options for handling such products. Similar exchange of hydrogen halides gas phase products for $CO_2$ and/or $H_2O$ can also be achieved using other types of basic materials and/or for other hydrogen halides.

Yet another option can be to have a separate halide removal stage after the thermal dehalogenation process but prior to the initial pyrolysis process. For example, a bed of CaO or another material that will sorb hydrogen halides can be used to sorb hydrogen halides that are evolved during thermal dehalogenation.

Initial Pyrolysis Stage

In various aspects, after any pre-processing and/or initial contaminant removal, the plastic feedstock can be fed into a fluidized bed pyrolysis reactor. The feedstock can be heated to a temperature between 400° C.-900° C., or 500° C.-900° C., or 400° C.-700° C., or 550° C. to 700° C., or 400° C.-500° C., for a reaction time to perform pyrolysis. The temperature can depend in part on the desired products. In aspects where a portion of the pyrolysis effluent will be exposed to a second thermal cracking stage, lower temperatures can be used in order to increase the yield of liquid phase products. In some aspects, the reaction time where the feedstock is maintained at or above 500° C. can be limited in order to reduce or minimize formation of coke. In some aspects, the reaction time can correspond to 0.1 seconds to 6.0 seconds, or 0.1 seconds to 5.0 seconds, or 0.1 seconds to 1.0 seconds, or 1.0 seconds to 6.0 seconds, or 1.0 seconds to 5.0 seconds. In other aspects, some types of reactors can have longer reaction times, such as a reaction time of 0.1 seconds to 120 seconds, or 10 seconds to 120 seconds, or 0.1 seconds to 90 seconds, or 10 seconds to 90 seconds. The pyrolyzed feedstock is cooled to below 500° C. at the end of the reaction time.

In some aspects, diluent steam can also be fed into the pyrolysis reactor. The steam also serves as a fluidizing gas.

In aspects where additional diluent steam is added, the weight ratio of steam to plastic feedstock can be between 0.3:1 to 10:1.

In some aspects, the pyrolysis reactor can correspond to a fluidized bed reactor. The fluidized bed can correspond to a fluidized bed of heat transfer particles. Sand is an example of a suitable type of particle for the fluidized bed, although any convenient type of particle can be used. During operation, heated heat transfer particles can be passed into the pyrolysis reactor to provide heat for the reaction. The feedstock can be introduced separately, to avoid melting of the plastic feedstock. A separate fluidizing gas can also be introduced at the bottom of the reactor to maintain the fluidized bed conditions. More generally, any convenient type of pyrolysis reactor can be used. Other examples of pyrolysis reactors include, but are not limited to, rotary kilns, stirred tank pyrolysis reactors, and screw/auger type pyrolysis reactors.

Due in part to the condition present in the pyrolysis reactor, substantially all of the effluent from the pyrolysis reactor can initially correspond to an effluent that is in the gas phase. As a result, the pyrolysis effluent can be withdrawn from the top of the reactor, while cooled heat transfer particles (such as cooled sand) can be withdrawn from a location near the bottom of the fluidized bed. After exiting from the pyrolysis reactor, the heat transfer particles can be separated from the vapor portions of the pyrolyzed effluent using a cyclone or another solid/vapor separator. Such a separator can also remove any other solids present after pyrolysis. Optionally, in addition to a cyclone or other primary solid/vapor separator, one or more filters can be included at a location downstream from the cyclone to allow for removal of fine particles that become entrained in the vapor phase. The cooled heat transfer particles can be passed into a regenerator to burn off coke and heat the particles, which are then returned to the reactor to provide the heat for pyrolysis. Depending on the amount of coke on the heat transfer particles, additional fuel can optionally be combusted in the regenerator to sufficiently increase the temperature of the heat transfer particles for maintenance of temperature in the fluidized bed of the pyrolysis reactor. The temperature of the heat transfer particles when leaving the regenerator can be greater than the desired temperature in the fluidized bed of the pyrolysis reactor by 50° C. or more, or 100° C. or more, such as up to 200° C. or possibly still greater. Optionally, a portion of the heat transfer particles can be purged prior to and/or after regeneration, in order to avoid build-up of other solids that may be present in the pyrolysis environment, such as solid halide particles. In such optional aspects, a make-up stream of heat transfer particles can be added to maintain a target level of particle inventory.

One of the difficulties with pyrolysis of plastic waste (and/or other polymers) can be handling chlorine that is evolved during pyrolysis, such as chlorine derived from pyrolysis of polyvinyl chloride and/or polyvinylidene chloride. In some aspects, the production of chlorine in the pyrolysis reactor can be mitigated by including a calcium source in the heat transfer particles, such as including calcium oxide particles. Within the pyrolysis environment, calcium oxide can react with chlorine generated during pyrolysis to form calcium chloride. This calcium chloride can then be purged from the system as part of a purge stream for the heat transfer particles. A corresponding make-up stream of fresh heat transfer particles can be introduced to maintain a desired amount of the heat transfer particles in the polyolefin pyrolysis stage. Calcium oxide particles could also be collected in a cyclone on the overhead of the reactor.

The pyrolysis effluent generated from pyrolysis of the plastic feedstock can include hydrocarbons with a range of boiling points. The pyrolysis effluent can generally include hydrocarbons ranging from $C_1$ compounds (methane) up to $C_{60}$ compounds or possibly compounds including still higher numbers of carbon atoms. In some aspects, $H_2$ can also be present in the pyrolysis effluent.

In some aspects, the pyrolysis can be operated under conditions that allow a substantial portion of the pyrolysis effluent to correspond to higher boiling compounds. For example, the pyrolysis effluent (according to ASTM D2887) can have a T50 distillation point of 100° C. or more, or 200° C. or more, or 250° C. or more. Additionally or alternately, the pyrolysis effluent can have a T70 distillation point of 450° C. or less, or a T80 distillation point of 450° C. or less, or a T90 distillation point of 450° C. or less.

After removing solids, the products can be cooled using a heat exchanger, a quench stream, or another convenient method, to a temperature of 300° C. to 400° C. to stop the reaction. Optionally, further cooling and/or quenching can also be performed. For example, the pyrolysis effluent can be sufficiently cooled so that a liquid phase fraction of the pyrolysis effluent includes a majority of the 350° C.+ products in the pyrolysis effluent. In some aspects, the cooling can be performed using a quench stream. The quench stream can be a recycle stream from another portion of the processing system, or a stream from a different processing system. For example, if the second thermal cracking process generates a distillate boiling range product (such as steam cracker gas oil), a portion of such a distillate boiling range product can be used as a quench stream. As another example, the quench stream can be the heavy portion of the pyrolysis product. After cooling the pyrolysis effluent to condense at least a portion of the effluent, the pyrolysis effluent can then be passed into a separator to separate a gas phase portion of the pyrolysis effluent from a liquid phase portion of the pyrolysis effluent.

Contaminant Removal Stage—Processing of Gas Phase Effluent Portion

Another type of contaminant removal stage that can be included in a chemical recycling configuration is a contaminant removal stage for removing contaminants from a portion of the effluent that remains in the gas phase after at least some cooling.

A variety of contaminant gases can be evolved under pyrolysis conditions, depending on the nature of the plastic feedstock. Such contaminant gases can include, but are not limited to, $NH_3$, HCl, HCN, alkyl halides, and various other light gases that can be formed from polymers that include atoms other than carbon and hydrogen. Examples of such additional light gases can include, but are not limited to, carbon oxides, methyl chloride, vinyl chloride, and ethyl chloride. Additionally or alternately, Hg, arsine, and phosphine can also potentially be present, depending on the nature of the plastic feedstock. An adsorbent bed (or group of adsorbent beds) is an example of a type of contaminant removal stage that can be used for removal of contaminants from a gas phase effluent portion. A water wash, optionally at acidic or basic conditions, is another example of a type of contaminant removal stage that can be used for removal of contaminants from a gas phase effluent portion.

Polymers can include a variety of contaminants that are present in larger quantities than crude oil fractions typically used as feed for steam cracking (or other types of pyrolysis). This can include contaminants such as chlorine that are substantially not present in typical crude oil fractions. This can also include contaminants such as oxygen and nitrogen that may be present in elevated amounts in a plastic feedstock. Some contaminants can correspond to components of the underlying polymer, such as the chlorine in polyvinyl chloride or the nitrogen in polyamide. Other contaminants can be present due to additives that are included when making a formulated polymer and/or due to packaging, adhesives, and other compounds that become integrated with the polyolefins after formulation. Such additives, packaging, adhesives, and/or other compounds can include additional contaminants such as chlorine, mercury, and/or silicon.

One type of contaminant removal can be a water wash. Optionally, the water wash can correspond to an amine wash and/or a caustic wash. Using an amine wash and/or a caustic wash can assist with removal of hydrogen halides as well as other contaminants, such as $CO_2$.

Additionally or alternately, chlorine removal can be accomplished using adsorbent beds for removal of hydrogen halides (e.g., HCl, HBr), and/or organic halides (such as methyl chloride, vinyl chloride, and/or ethyl chloride). Examples of suitable adsorbent bed particles for removal of halogens/halides include calcium oxide, magnesium oxide, zinc oxide, and combinations thereof.

Adsorbent beds can also be used for removal of other types of contaminants. For example, another type of adsorbent bed can correspond to an adsorbent bed for removal of ammonia. In addition to nitrogen-containing polymers such as polyamides, various types of polymer additives can include nitrogen. In a pyrolysis environment, a portion of this nitrogen can be converted to HCN, acetonitrile, ammonia, and/or small amines. Various types of adsorbents are available for removal of such nitrogen compounds, such as molecular sieve-based adsorbents.

Yet another example for use of adsorbent beds can be to handle gas phase contaminants such as arsine, mercury, and/or phosphine. Examples of adsorbent beds for Hg removal include adsorbent beds including refractory oxides with transition metals optionally supported on the surface, such as the oxides and metals used in demetallization catalysts or a spent hydrotreating catalysts.

Still another potential contaminant is CO. If a sufficient amount of a polyether or polyester is included in the plastic feedstock, a substantial amount of CO and/or $CO_2$ may be formed under the initial pyrolysis conditions. As noted above, $CO_2$ can be removed by using an amine or caustic wash. However, CO typically is not removed in such a wash stage. Instead, CO can be removed by including a methanation process as part of a contaminant removal stage. Methanation can convert CO and/or $CO_2$ into methane via addition of hydrogen.

After removal of contaminants, there are several options for handling the gas phase portion of the effluent. In some aspects, a portion of the gas phase portion of the effluent can be recycled to the pyrolysis reactor, such as for use as a fluidizing gas for the fluidized bed pyrolysis process and/or as a fuel gas for providing heat. It is noted that it would be possible to recycle a portion of the gas phase portion of the effluent to the pyrolysis process without performing contaminant removal, but such recycle would have a tendency to result in build-up of higher concentrations of contaminants within the system.

Additionally or alternately, a portion of the gas phase portion of the effluent can be included as part of the products that are passed into one or more additional (conventional) processes. The gas phase portion of the effluent can contain a variety of components that are suitable for further processing. For example, some types of steam crackers are designed to operate with lower boiling feedstocks, such as using ethane or other $C_4$ hydrocarbons as the feed for steam cracking. Additionally, the gas phase portion of the effluent may still be at a temperature greater than 25° C. after the gas-liquid separation. Thus, some higher boiling hydrocarbons, such as $C_5$-$C_8$ hydrocarbons and/or other naphtha boiling range compounds, may also be present in the gas phase portion of the effluent.

Further additionally or alternately, after contaminant removal, a portion of the gas phase portion of the pyrolysis effluent can be passed into the downstream processing train for processing of the gas phase portion of the effluent from the one or more additional (conventional) processes. For example, if at least a portion of the pyrolysis effluent (such as at least a portion of the liquid phase effluent) is passed into a steam cracking process, some of the gas phase portion of the pyrolysis effluent can be added to the gas phase portion of the effluent from the steam cracking process. One option for adding a gas phase portion of the pyrolysis effluent to a gas phase portion of a steam cracking effluent can be to combine the portions in the process gas compressor for the steam cracking effluent processing train.

Contaminant Removal Stage—Processing of Liquid Phase Effluent Portion

Still another type of contaminant removal stage that can be included in a chemical recycling configuration is a contaminant removal stage for removing contaminants from a liquid phase portion of the effluent that is formed after at least some cooling. For liquid phase contaminant removal, a contaminant removal stage can be included as part of a liquid recycle loop and/or as a contaminant removal stage prior to starting additional (conventional) processing of a liquid portion of the effluent.

A contaminant removal stage as part of a liquid recycle loop can be used to reduce or minimize the content of various contaminants in the liquid phase portion of the effluent. This can include contaminants such as arsenic, mercury, silicon, and phosphorus. It is noted that alkylated forms of arsenic, mercury, and phosphorus can end up in the liquid portion of the pyrolysis effluent, while non-alkylated forms can tend to end up in the gas phase portion of the pyrolysis effluent.

One type of contaminant removal process can be a mercury removal process, such as passing the liquid recycle through a fixed bed mercury trap. The elevated temperatures present in a pyrolysis reaction environment can convert any mercury present in the polyolefin feed into elemental mercury. Such elemental mercury can then be removed using an adsorbent bed. It is noted that some adsorbent beds suitable for mercury removal can also be suitable for silicon removal. Examples of such adsorbent beds include adsorbent beds including refractory oxides with transition metals optionally supported on the surface, such as the oxides and metals used in demetallization catalysts or a spent hydrotreating catalysts. Additionally or alternately, separate adsorbent beds can be used for silicon and mercury removal, or separate adsorbents for silicon removal and mercury removal can be included in a single adsorbent bed. Examples of suitable mercury adsorbents and silicon adsorbents can include, but are not limited to, molecular sieves that are suitable for adsorption of mercury and/or silicon.

Adsorbent beds, such as fixed bed traps, can also be used for removal of alkylated arsenic and/or phosphorus compounds.

Another type of contaminant removal can be performed based on additional distillation of the liquid portion of the pyrolysis effluent. For example, in some aspects, after contaminant removal, a fraction of the liquid portion of the pyrolysis effluent can be used as a feed for steam cracking. Due to the nature of a steam cracking process, it is beneficial to remove higher boiling components, such as 450° C.+ components, from a feedstock prior to introducing the feedstock into the steam cracker. In order to achieve this, a vacuum distillation or another type of separation can be performed to separate the liquid portion of the effluent into a bottoms portion containing a majority of the 450° C.+ compounds and a lower boiling portion. In this type of configuration, a majority of the metals in the liquid portion of the pyrolysis effluent will be separated into the bottoms portion, so that the bottoms portion ends up having a higher metal concentration. Such a bottoms portion can optionally be removed from the processing system in order to remove the metals. Additionally or alternately, such a bottoms portion can be recycled to the pyrolysis stage, optionally after passing through one or more adsorbent beds for removal of metal contaminants.

It is noted that for the liquid phase portion of the pyrolysis effluent, distillation stages and contaminant removal stages can be organized in any convenient manner. Thus, distillation stages for at least partial separation of the liquid phase portion of the pyrolysis effluent can be included prior to, between, and/or after contaminant removal stages.

For a contaminant removal stage prior to passing a liquid portion of the effluent into additional processing stages, any of the contaminant removal processes for use in a liquid recycle loop can be used. Additionally, after removal of chlorine and/or metals, hydroprocessing can optionally be used to remove any remaining sulfur, nitrogen, and/or oxygen from the liquid portion of the effluent prior to further processing. By delaying hydroprocessing until after substantial contaminant removal has already been performed, a variety of advantages can be achieved. First, the volume of feed that is hydroprocessed can be reduced, as a substantial portion of the pyrolysis effluent can be processed as a gas phase effluent rather than as a liquid effluent. Additionally, any recycled portions of the liquid effluent are not hydroprocessed. This can reduce or minimize the amount of hydrogen that is consumed by reactions other than removal of heteroatoms. Another advantage of delaying the exposure of the liquid effluent to hydroprocessing conditions is that damage to the hydroprocessing catalyst and/or reactor due to contaminants can be reduced or minimized.

In some aspects, after contaminant removal, the liquid phase portion of the pyrolysis effluent can have a halide content (e.g., HCl, $CH_3Cl$, HBr, other halide compounds) of 100 wppm or less, or 50 wppm or less, or 25 wppm or less, or 20 wppm or less, or 15 wppm or less, or 10 wppm or less, or 1.0 wppm or less, such as down to 0.01 wppm or possibly still lower. As additional examples, in some aspects the halide content can be 0.01 wppm to 100 wppm, or 10 wppm to 100 wppm, or 25 wppm to 100 wppm, or 1.0 wppm to 50 wppm, or 10 wppm to 50 wppm, or 25 wppm to 50 wppm, or 0.01 wppm to 25 wppm, or 1.0 wpmp to 25 wppm, or 10 wppm to 25 wppm, or 0.1 wppm to 10 wppm, or 0.01 wppm to 1.0 wppm. Additionally or alternately, the liquid phase portion of the pyrolysis effluent can have a chloride content (e.g., HCl, $CH_3Cl$) of 100 wppm or less, or 50 wppm or less, or 25 wppm or less, or 20 wppm or less, or 15 wppm or less, or 10 wppm or less, or 1.0 wppm or less, such as down to 0.01 wppm or possibly still lower. As additional examples, in some aspects the chloride content can be 0.01 wppm to 100 wppm, or 10 wppm to 100 wppm, or 25 wppm to 100 wppm, or 1.0 wppm to 50 wppm, or 10 wppm to 50 wppm, or 25 wppm to 50 wppm, or 0.01 wppm to 25 wppm, or 1.0 wpmp to 25 wppm, or 10 wppm to 25 wppm, or 0.1 wppm to 10 wppm, or 0.01 wppm to 1.0 wppm.

Configuration Example

In various aspects, a chemical recycling process configuration can be formed by integrating at least one pyrolysis stage and a plurality of contaminant removal stages with one or more additional conventional petrochemical processes. The chemical recycling process can also include one or more separation stages prior to the conventional petrochemical processes to assist with contaminant removal and/or to assist with separating fractions out to be directed to appropriate contaminant removal stages.

Figure 3:
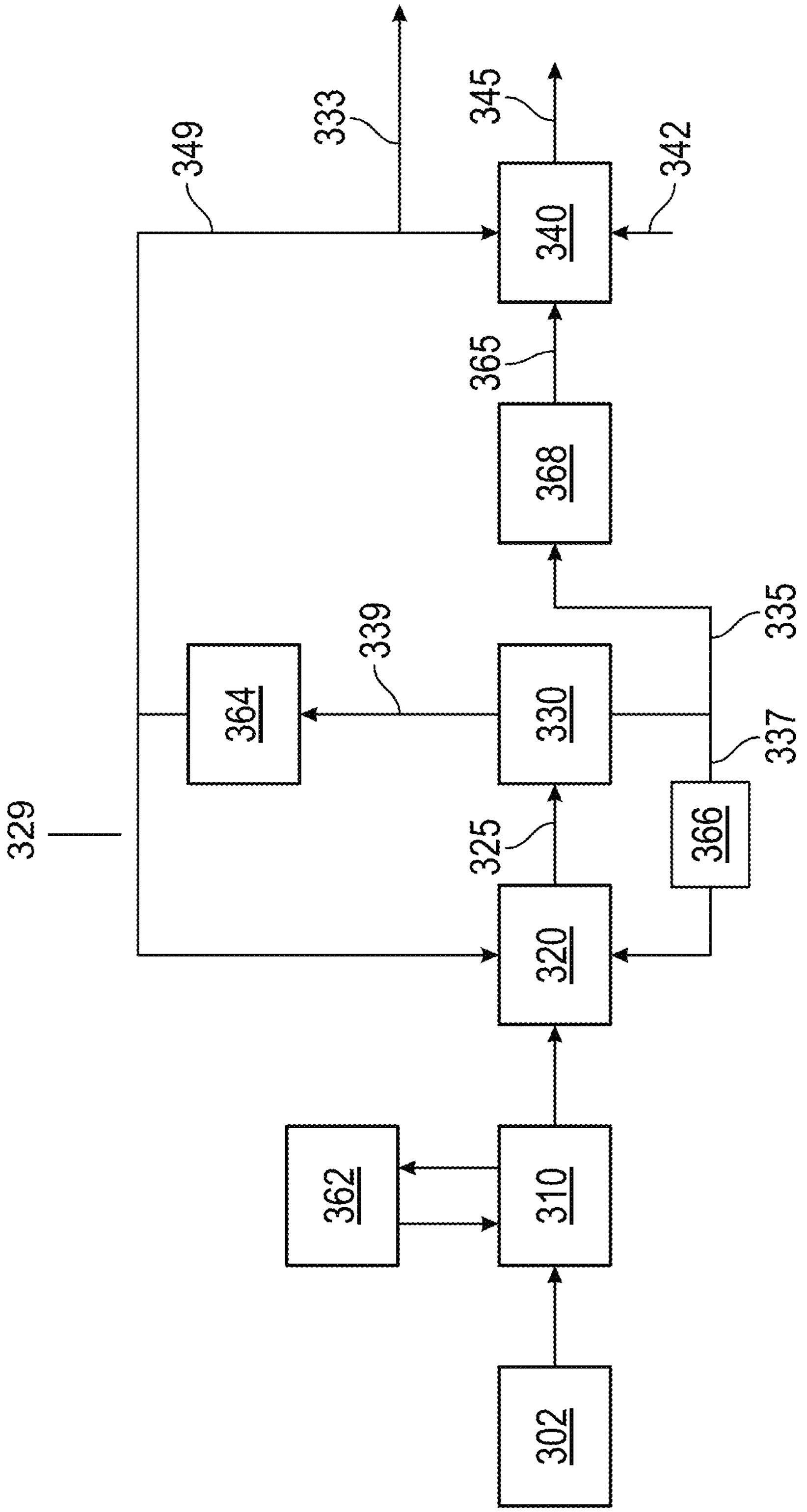
FIG. 3 shows an example of a chemical recycling process based on integration of a pyrolysis stage and one or more contaminant removal stages with one or more downstream conventional petrochemical processes.

FIG. 3 shows an example of a chemical recycling process based on integration of a pyrolysis stage and one or more contaminant removal stages with one or more downstream conventional petrochemical processes. In the example shown in FIG. 3, the integrated chemical recycling process includes a steam cracking stage as a downstream conventional petrochemical process, but any other convenient type of processing can be performed, such as other types of pyrolysis, catalytic cracking (such as fluidized catalytic cracking), and/or hydroprocessing.

In the example configuration shown in FIG. 3, four separate contaminant removal stages 362, 364, 366, and 368 are shown. Individually, each of stage 362, stage 364, stage 366, and stage 368 are optional. Depending on the configuration, any one of the stages can be present, or any two, or any three, or up to all four can be present in a configuration. Each of stage 362, 364, 366, and 368 can correspond to one or more contaminant removal processes (e.g., adsorbent beds, separations) depending on the configuration. It is further noted that a contaminant removal stage can correspond to a single type of removal process or a plurality of processes.

In the example configuration shown in FIG. 3, a feed of solid recycled plastic 302 can enter into a chemical recycling process after undergoing sufficient physical processing 310. The physical processing 310 can include, but is not limited to, grinding, sorting, washing, compression, and/or pelletization. During physical processing 310, some optional contaminant removal 362 can also be performed. It is noted that contaminant removal 362 can include a thermal dehalogenation stage. The pre-treated recycled material is then fed to a conversion stage 320, such as a fluidized bed thermal pyrolysis stage or another type of pyrolysis stage. The conversion stage produces a conversion effluent 325. The conversion effluent 325 can be sent to a separation stage 330 where the conversion effluent 325 is condensed as part of separating the conversion effluent to form a vapor effluent stream 339 and a liquid effluent stream 335.

For the liquid effluent stream 335, a portion 337 of the liquid effluent stream 335 can optionally be recycled back to the conversion stage 320. In aspects where a portion 337 of the liquid effluent stream 335 is recycled, the liquid recycle portion 337 can optionally be passed into contaminant removal stage 366 prior to returning to conversion stage 320. The rest of liquid effluent stream 335 can be passed into optional contaminant removal stage 368 to form a reduced contaminant liquid product 365.

The vapor effluent 339 can be passed into optional contaminant removal stage 364. It is noted that the overhead from contaminant removal stage 362 can optionally also be passed into contaminant removal stage 364. After the optional contaminant removal 364, depending on the aspect, the vapor effluent can be used as a vapor recycle portion 329 that is returned to conversion stage 320, and/or the vapor effluent can be used as a vapor product stream 349, and/or the vapor effluent can be added 333 to the processing train for processing of the gas phase portion of the effluent/products 345 generated by petrochemical process 340. In FIG. 3, the optional vapor product stream 349 is shown as being introduced into petrochemical process 340 (such as a steam cracker).

The reduced contaminant liquid product 365, and any optional vapor product stream 349, can then be passed into a petrochemical process 340. The reduced contaminant liquid product 365 and/or optional vapor product stream 349 can optionally be combined with one or more conventional co-feeds 342 for processing in petrochemical process 340. This can allow for production of one or more products 345. Examples of petrochemical processes can include, but are not limited to, olefin generation with a crude cracker, olefin generation with a naphtha cracker, olefin generation with a liquid cracker, olefin generation with a gas cracker, other forms of pyrolysis and/or catalytic cracking, hydroprocessing, and/or gas separation. Optionally, at least a portion 333 of vapor product stream 349 can be added to a downstream location in the processing of one or more products 345.

A configuration such as FIG. 3 provides examples of both direct fluid communication and indirect fluid communication between elements of the configuration. For example, the gas-liquid separation stage 330 shown in FIG. 3 is in direct fluid communication with conversion stage (such as a pyrolysis reactor) 320 and contaminant removal stage 368. In aspects where contaminant removal stage 368 is included in a configuration, gas-liquid separation stage 330 can be in indirect fluid communication with petrochemical process 340 via contaminant removal stage 368.

Further Processing Example—Olefin Production (Via Steam Cracking)

Steam cracking is an example of a process that can be used for additional processing of a portion of the effluent from initial pyrolysis. Steam cracking can result in production of substantial volumes of olefins, so steam cracking is an example of additional processing that can allow for complete "chemical recycling" of polymers back into raw building blocks for new polymer formation.

In various aspects, the input flow to a steam cracking process can correspond to a mixture of a portion of effluent from the initial pyrolysis process and a conventional liquid steam cracker feed. In some aspects, the conventional liquid steam cracker feed can be mixed with the portion of the effluent from the first pyrolysis process prior to entering the steam cracking stage. In other aspects, mixing can occur within the steam cracking stage. More generally, any convenient type of additional processing can be performed using a mixture of effluent from the initial pyrolysis process and one or more co-feeds that are appropriate to the nature of the additional processing.

In some aspects, the input flow to a steam cracking process (and/or other conversion process) can have a halide content (e.g., HCl, $CH_3Cl$, HBr, other halide compounds) of 25 wppm or less, or 20 wppm or less, or 15 wppm or less, or 10 wppm or less, or 5.0 wppm or less, or 1.0 wppm or less, such as down to 0.01 wppm or possibly still lower. As additional examples, in some aspects the halide content can be 0.01 wppm to 25 wppm, or 1.0 wppm to 25 wppm, or 5.0 wppm to 25 wppm, or 0.01 wppm to 10 wppm, or 1.0 wppm to 10 wppm, or 0.1 wppm to 5.0 wppm, or 0.01 wppm to 1.0 wppm. Additionally or alternately, the input flow to a steam cracking process (and/or other conversion process) can have a chloride content (e.g., HCl, $CH_3Cl$) of 25 wppm or less, or 20 wppm or less, or 15 wppm or less, or 10 wppm or less, or 5.0 wppm or less, or 1.0 wppm or less, such as down to 0.01 wppm or possibly still lower. As additional examples, in some aspects the chloride content can be 0.01 wppm to 25 wppm, or 1.0 wppm to 25 wppm, or 5.0 wppm to 25 wppm, or 0.01 wppm to 10 wppm, or 1.0 wppm to 10 wppm, or 0.1 wppm to 5.0 wppm, or 0.01 wppm to 1.0 wppm.

Conventionally, a liquid feed for steam cracking can correspond to any type of liquid feed (i.e., feed that is liquid at 20° C. and 100 kPa-a, as defined herein). Examples of suitable reactor feeds can include whole and partial crudes, naphtha boiling feeds, distillate boiling range feeds, resid boiling range feeds (atmospheric or vacuum), or combinations thereof. Additionally or alternately, a suitable feed can have a T10 distillation point of 100° C. or more, or 200° C. or more, or 300° C. or more, or 400° C. or more, and/or a suitable feed can have a T95 distillation point of 450° C. or less, or 400° C. or less, or 300° C. or less, or 200° C. or less. It is noted that the feed for steam cracking can be fractionated to remove a bottoms portion prior to performing steam cracking so that the feed entering the reactor has a T95 distillation point of 450° C. or less. The distillation boiling range of a feed can be determined, for example, according to ASTM D2887. If for some reason ASTM D2887 is not suitable, ASTM D7169 can be used instead. Although certain aspects of the invention are described with reference to particular feeds, e.g., feeds having a defined T95 distillation point, the invention is not limited thereto, and this description is not meant to exclude other feeds within the broader scope of the invention.

A steam cracking plant typically comprises a furnace facility for producing steam cracking effluent and a recovery facility for removing from the steam cracking effluent a plurality of products and by-products, e.g., light olefin and pyrolysis tar. The furnace facility generally includes a plurality of steam cracking furnaces. Steam cracking furnaces typically include two main sections: a convection section and a radiant section, the radiant section typically containing burners. Flue gas from the radiant section is conveyed out of the radiant section to the convection section. Hydrocarbon is introduced into tubular coils (convection coils) located in the convection section. Steam is also introduced into the coils, where it combines with the hydrocarbon to produce a steam cracking feed. The combination of indirect heating by the flue gas and direct heating by the steam leads to vaporization of at least a portion of the steam cracking feed's hydrocarbon component. The steam cracking feed containing the vaporized hydrocarbon component is then transferred from the convection coils to tubular radiant tubes located in the radiant section. Indirect heating of the steam cracking feed in the radiant tubes results in cracking of at least a portion of the steam cracking feed's hydrocarbon component. Steam cracking conditions in the radiant section, can include, e.g., one or more of (i) a temperature in the range of 760° C. to 880° C., (ii) a pressure in the range of from 1.0 to 5.0 bars (absolute), or (iii) a cracking residence time in the range of from 0.10 to 0.5 seconds.

Steam cracking effluent is conducted out of the radiant section and is quenched, typically with water or quench oil. The quenched steam cracking effluent is conducted away from the furnace facility to the recovery facility, for separation and recovery of reacted and unreacted components of the steam cracking feed. The recovery facility typically includes at least one separation stage, e.g., for separating from the quenched effluent one or more of light olefin, steam cracker naphtha, steam cracker gas oil, steam cracker tar, water, light saturated hydrocarbon, and molecular hydrogen.

Steam cracking feed typically comprises hydrocarbon and steam, such as 10.0 wt % or more hydrocarbon, based on the weight of the steam cracking feed, or 25.0 wt % or more, or 50.0 wt % or more, or 65 wt % or more, and possibly up to 80.0 wt % or possibly still higher. Although the hydrocarbon can comprise one or more light hydrocarbons such as methane, ethane, propane, butane etc., it can be particularly advantageous to include a significant amount of higher molecular weight hydrocarbon. Using a feed including higher molecular weight hydrocarbon can decrease feed cost, but can also increase the amount of steam cracker tar in the steam cracking effluent. In some aspects, a suitable steam cracking feed can include 10 wt % or more, or 25.0 wt % or more, or 50.0 wt % or more (based on the weight of the steam cracking feed) of hydrocarbon compounds that are in the liquid and/or solid phase at ambient temperature and atmospheric pressure, such as up to having substantially the entire feed correspond to heavier hydrocarbons.

The hydrocarbon portion of a steam cracking feed can include 10.0 wt % or more, or 50.0 wt % or more, or 90.0 wt % or more (based on the weight of the hydrocarbon) of one or more of naphtha, gas oil, vacuum gas oil, waxy residues, atmospheric residues, residue admixtures, or crude oil, such as up to substantially the entire feed. Such components can include those containing 0.1 wt % or more asphaltenes. When the hydrocarbon includes crude oil and/or one or more fractions thereof, the crude oil is optionally desalted prior to being included in the steam cracking feed. A crude oil fraction can be produced by separating atmospheric pipestill ("APS") bottoms from a crude oil followed by vacuum pipestill ("VPS") treatment of the APS bottoms. One or more vapor-liquid separators can be used upstream of the radiant section, e.g., for separating and conducting away a portion of any non-volatiles in the crude oil or crude oil components. In certain aspects, such a separation stage is integrated with the steam cracker by preheating the crude oil or fraction thereof in the convection section (and optionally by adding of dilution steam), separating a bottoms steam comprising non-volatiles, and then conducting a primarily vapor overhead stream as feed to the radiant section.

After performing secondary thermal cracking (such as steam cracking), olefins can be recovered from the secondary thermal cracking effluent by any convenient method. For example, various separations can be performed to separate $C_2$, $C_3$, $C_4$ and/or $C_5$ olefins from the secondary thermal cracking effluent.

In some alternative aspects, at least a portion of the gas phase effluent can be passed into the product recovery train for the secondary thermal cracker. For example, a $C_2$-$C_5$ portion of the gas phase pyrolysis effluent can be passed into the recovery train for the secondary thermal cracker without being passed through the secondary thermal cracker. This can allow for recovery of olefins that are made in the pyrolysis process, while still allowing the remaining portion(s) of the gas phase and/or liquid phase pyrolysis effluent to be passed into the secondary thermal cracker for additional olefin production. In this type of configuration, it is noted that a supplemental quench tower can optionally be used to perform some contaminant removal prior to combining the gas phase pyrolysis effluent with the recovery train for the secondary thermal cracker. For example, a supplemental quench tower can allow ammonia to be removed using a water wash prior to combining the pyrolysis effluent with steam cracking effluent.

Stages for Processing of Products from Secondary Thermal Cracking (e.g., Steam Cracking)

After performing steam cracking (and/or another type of secondary thermal cracking), one or more contaminant removal stages can be incorporated into the steam cracking process train for processing of the steam cracker effluent. An adsorbent bed (or group of adsorbent beds) an example of a type of contaminant removal stage.

One type of contaminant removal can be use of a water wash, optionally at acidic or basic conditions. Optionally, the water wash can correspond to an amine wash and/or a caustic wash. Using an amine wash and/or a caustic wash can assist with removal of chlorine as well as other contaminants, such as $CO_2$.

Another form of contaminant removal can be achieved based on pH control within the quench tower(s). Based on additives for pH control, at least a portion of any $NH_3$ in the pyrolysis effluent (and/or in the steam cracker effluent) can be converted to ammonia salts. Such salts can then be retained in the quench water and/or removed via separate water wash.

Additionally or alternately, an additional adsorbent bed can be included for removal of various alkyl halides and hydrogen halides. Such hydrogen halides and alkyl halides can include, but are not limited to, HCl, methyl chloride, ethyl chloride, vinyl chloride, HBr, methyl bromide, $C_2F_4$, $C_2H_2F_2$, $C_3F_6$, HI, methyl iodide, and/or other halide compounds. For example, an adsorbent bed for removal of chlorine compounds and/or halide compounds can be included after the supplemental quench tower. Examples of suitable adsorbent bed particles for chlorine removal (and/or halogen removal) include calcium oxide, magnesium oxide, zinc oxide, and combinations thereof.

It is noted that in some aspects, substantially all chlorides and/or halides can be removed from the input flow that is introduced into the steam cracking process, so that substantially no chlorides and/or halides are present after steam cracking. In other aspects, some chlorides and/or halides can remain in the input flow that is introduced into steam cracking. This can optionally also include chlorides and/or halides that are included in any conventional feedstock that is used as a co-feed for a steam cracking process. In still other aspects, one or more types of chlorides and/or halides present in the initial feedstock for pyrolysis can be in a form that is not readily removed by the processing stage prior to steam cracking. In such aspects, the effluent from the steam cracking process can include 5.0 vppm or more of chloride and/or halide compounds, or 10 vppm or more, or 20 vppm or more, such as up to 200 vppm or possibly still higher. In such aspects, the chloride and/or halide compounds in the steam cracking effluent can correspond to chloride and/or halide compounds formed during steam cracking, chloride and/or halide compounds formed prior to steam cracking, or a combination thereof. When such chloride and/or halide compounds are present, water washing, amine-water washing, and/or adsorbent beds are examples of contaminant removal processes that can remove the compounds. After performing contaminant removal on the effluent, separations can be used to a) form an ethylene stream containing 99 vol % or more ethylene and 1.0 wppm or less, or 500 wppb or less, or 200 wppb or less, or 100 wppb or less, of one or more halide compounds, such as down to containing substantially no halide compounds and/or b) to form a propylene stream containing 99 vol % or more propylene and 1.0 wppm or less, or 500 wppb or less, or 200 wppb or less, or 100 wppb or less, of one or more halide compounds, such as down to containing substantially no halide compounds.

Still another type of adsorbent bed can correspond to an adsorbent bed for removal of ammonia. In addition to nitrogen-containing polymers such as polyamides, various types of polymer additives can include nitrogen. In a pyrolysis environment, a portion of this nitrogen can be converted to ammonia. Various types of adsorbents are available for removal of ammonia, such as molecular sieve base adsorbents. Still further nitrogen removal can be performed by adding a nitrogen adsorbent (such as a molecular sieve suitable for ammonia adsorption) to one or more process gas driers located downstream from the process gas compressor.

It is noted that the presence of some ammonia and/or amines can potentially be beneficial for neutralizing hydrogen halides present in the pyrolysis effluent. For example, ammonia can react with HCl to ammonium chloride, a solid salt that can be readily removed from a reaction system in a variety of manners.

Still other contaminant removal stages can be included for processing of the combined effluents. For example, silicon is commonly found in additives used in polymer formulation. After pyrolysis, the silicon typically is separated into a liquid product. A silicon trap can be added to the steam cracking process train to remove silicon from the liquid steam cracker effluent after it exits from the quench tower.

A fixed bed mercury trap can also be included in the steam cracking process train. The elevated temperatures present in a pyrolysis reaction environment can convert any mercury present in the polyolefin feed into elemental mercury. Such elemental mercury can then be removed using an adsorbent bed. It is noted that some adsorbent beds suitable for mercury removal can also be suitable for silicon removal. Examples of such adsorbent beds include adsorbent beds including refractory oxides with transition metals optionally supported on the surface, such as the oxides and metals used in demetallization catalysts or a spent hydrotreating catalysts. Additionally or alternately, separate adsorbent beds can be used for silicon and mercury removal, or separate adsorbents for silicon removal and mercury removal can be included in a single adsorbent bed. Examples of suitable mercury adsorbents and silicon adsorbents can include, but are not limited to, molecular sieves that are suitable for adsorption of mercury and/or silicon.

Yet other contaminant removal stages can correspond to contaminant removal that may already be present in a steam cracking process train. For example, CO can be removed by methanation of CO at a downstream location. Additional ammonia and/or oxygen removal stages can also be included.

Configuration Examples

Figure 2:
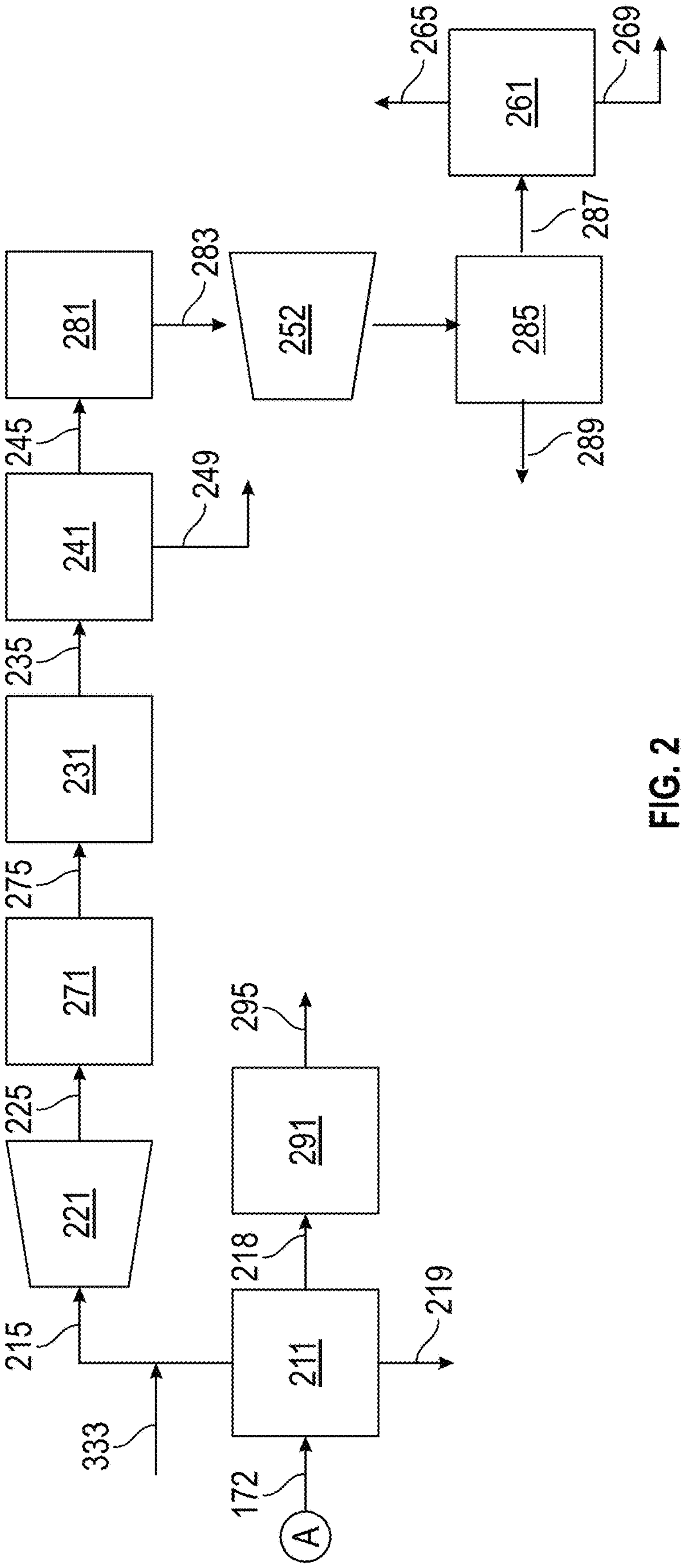
FIG. 2 shows an example of another portion of an integrated process train for pyrolysis and processing of a plastic feedstock.

FIGS. 1 and 2 show additional details for a configuration that integrates polyolefin pyrolysis with a steam cracking process train. In FIG. 1, a feed for steam cracking 165 (such as reduced contaminant liquid product 365 from FIG. 3) is passed into a steam cracking reactor 140. In the example shown in FIG. 1, any optional removal of high molecular weight fractions from the feed 165 has already been performed. Optionally, feed 165 can be combined with steam 142 prior to entering the steam cracking reactor 140. The steam cracking reactor 140 can be operated to produce lower molecular weight hydrocarbons, such as $C_2$-$C_4$ olefins. Under such steam cracking conditions, the steam cracking reactor can also produce various fractions, such as steam cracked naphtha, steam cracker gas oil, and steam cracker tar.

The steam cracker effluent 145 from the steam cracking reactor 140 can then be passed into, for example, a quench stage 150 where the steam cracker effluent 145 is indirectly cooled with water and/or mixed with quench oil (such as optional quench oil 177) to cool the effluent. The quench oil can correspond to, for example, a fraction from the primary fractionator 170, such as a steam cracker gas oil fraction or a bottoms fraction, depending on the configuration. The quenched effluent 155 can then be passed into primary fractionator 170. Optionally, the quenched effluent can be passed through a tar knockout drum or other separator (not shown) for removal of steam cracker tar prior to entering the primary fractionator 170.

In the example shown in FIG. 1, the primary fractionator 170 can generate a bottoms product 179 (such as steam cracker tar), one or more intermediate products (such as quench oil 177 and/or steam cracker gas oil 175), and an overhead product 172 that includes gas phase components (including olefin monomers) and steam cracker naphtha. A portion 177 of the intermediate products can be used as a quench oil. The overhead product 172 can be further processed, as shown in FIG. 2. Optionally, a hydrotreating unit (not shown) can be used to hydrotreat at least a portion of bottoms product 179. Prior to such hydrotreating (such as hydrogenation), a guard bed can optionally be used to allow for removal of contaminants such as silica and/or metals that are contained in the bottoms product 179.

FIG. 2 shows the portion of the steam cracking process train that handles separation of olefin monomers. The fraction 172 from FIG. 1 can be passed into a quench tower 211. This can remove water 219 while forming a naphtha fraction 218 and a $C_{5-}$ fraction 215. Optionally, a $C_{5-}$ vapor product stream 333 derived from the initial pyrolysis stage (such as a portion of vapor product stream 349 from FIG. 3) can also be passed into quench tower 211 and/or added to the overhead stream 215 from quench tower 211. The naphtha fraction 218 can then be passed into a hydrotreater 291 and/or another type of silicon removal stage to form a naphtha product 295. The $C_{5-}$ fraction 215 can be compressed in a process gas compressor 221. It is noted that in some aspects, vapor product stream 333 and/or fraction 215 can correspond to $C_{4-}$ fractions instead of $C_{5-}$ fractions, in order to incorporate more of the products into the naphtha fraction 218.

It is noted that the configuration in FIG. 1 and FIG. 2 corresponds to having a separate fractionator 170 and quench tower 211. It is noted that some types of fractionation stages can allow fractionator 170 and quench tower 211 to be integrated into a single unit.

In the example shown in FIG. 2, after compression, the compressed stream 225 can be passed through a wash stage 271, such as a water wash, a caustic wash, or an amine wash, to remove $CO_2$, hydrogen halides (such as HCl), alkyl halides, and/or $NH_3$. The wash stage effluent 275 can then be passed into process gas driers 231. The process gas driers 231 can optionally but preferably include a contaminant removal stage. For example, process gas driers 231 can include a molecular sieve or another type of structure that can serve as a mercury trap. Additionally or alternately, process gas driers 231 can include one or more ammonia removal beds.

The effluent 235 from the process gas driers/contaminant removal 231 can then be separated to form fractions containing the component monomers. In the example shown in FIG. 2, this process can be started by passing effluent 235 into a de-ethanizer 241. De-ethanizer 241 can form a $C_{3+}$ product 249 and a $C_{2-}$ product 245. The $C_{3+}$ product 249 can undergo further separations to allow for recovery of $C_3$ olefins and $C_4$ products. The $C_{2-}$ product 245 can be optionally passed into an acetylene conversion stage 281. After optional acetylene conversion, the acetylene conversion product 283 can be passed into cold box 252. Cold box 252 can separate $H_2$ and methane. At least a portion of the stream(s) from cold box 252 can then be passed into demethanizer stage 285 for removal of a stream 289 that can include $CH_4$, CO and $H_2$. The remaining stream 287, which includes $C_2$ components, can be passed into separation stage 261 for separation of ethane 269 from ethylene 265.

A series of separations can similarly be performed on the $C_{3+}$ product. For example, the $C_{3+}$ product can be passed into a depropanizer to form a $C_{4+}$ product and a $C_3$ product. The $C_3$ product can then be split to form a $C_3$ paraffin stream and a $C_3$ olefin stream. It is noted that if methyl chlorides are present in the $C_3$ product, such methyl chlorides tend to concentrate in the $C_3$ paraffin stream. Similarly, one or more separations can be performed on the $C_{4+}$ product. In some aspects, the separation(s) can be controlled so that ethyl chloride is separated into a $C_4$ paraffin product while vinyl chloride is separated into a butadiene product. This can reduce, minimize, or eliminate the presence of chlorides in a butene product.

It is noted that the configuration shown in FIG. 2 corresponds to starting with a de-ethanizer as the first of a series of separation stages for forming component monomers. In other aspects, the separation into component monomers can be performed in any convenient order. For example, instead of starting with a de-ethanizer, in another configuration the first separator can correspond to a depropanizer. In this type of configuration, the first separation forms a $C_{3-}$ stream and a $C_{4+}$ stream, as opposed to the configuration shown in FIG. 2 where the initial separation forms a $C_{2-}$ stream and a $C_{3+}$ stream.

In a configuration where the first separator corresponds to a depropanizer, the $C_{3-}$ stream can first be passed into an acetylene converter. The effluent from the acetylene convertor can then be passed to a chill train that includes a cold box and a demethanizer. $H_2$ and $CH_4$ are separated and $C_2$ and $C_3$ molecules are passed on to a de-ethanizer. The de-ethanizer overhead ($C_2$ stream) can go through one or more optional treatment steps and then to a $C_2$ splitter to separate ethane and ethylene.

The deethanizer bottoms ($C_3$ stream) goes to a methylacetylene and propadiene (MAPD) converter where chloride can get partially removed, such as by including an adsorbent bed at the top of the catalyst beds. The product of the MAPD converter eventually goes to $C_3$ splitter to separate propylene and propane. As noted above, methyl chloride present in the $C_3$ stream can end up in a propane product. Additionally, the depropanizer bottoms ($C_{4+}$ stream) goes to a debutanizer. Ethyl chloride and vinyl chloride can be separated into a debutanizer overhead. Ethyl chloride can then be separated out with $C_4$ paraffins while vinyl chloride is separated out with butadiene.

It is noted that if any of the $C_2$, $C_3$, and/or $C_4$ products ends up with an alkyl chloride content that is higher than a target or desired value, one option for reducing the chloride content can be to recycle at least a portion of such a product back to the steam craking stage.

Polymer Formation

After sufficient separation steps, at least one of a high purity ethylene product stream and/or a high purity propylene product stream can be formed from the gas phase products from the steam cracker (or other second conversion stage). For example, a high purity product stream can include 99.0 wt % or more (such as up to 100 wt %) of ethylene or propylene. Such a high purity stream can then be used in an oligomerization reaction/polymerization reaction, such as for production of polymers.

An example of an oligomerization reaction is a slurry polymerization reaction, such as the slurry polymerization process described in U.S. Pat. No. 7,146,130, which is incorporated herein by reference for the limited purpose of describing a slurry polymerization process. An example of a suitable type of catalyst in a slurry polymerization process can be a Ziegler-Natta catalyst. Another example of oligomerization reaction is a continuous solution polymerization process, such as the process described in U.S. Pat. No. 9,815,913, which is incorporated herein by reference for the limited purpose of describing a continuous solution polymerization process. An example of a suitable type of catalyst for use in a continuous solution polymerization process is a metallocene catalyst. Catalysts such as Ziegler-Natta type catalysts or metallocene type catalysts can be sensitive to the presence of halide compounds in the oligomerization environment. Thus, using an ethylene and/or propylene stream derived from a plastic waste feedstock that contained substantial amounts of halide-containing polymers would conventionally be avoided. However, but processing a plastic feedstock using the methods described herein, olefins derived from a plastic feedstock that includes chlorine-containing (or other halogen-containing) polymers can be used for synthesis of new polymers.

Example—Formation of Solid Dechlorination Product

Several calcium compounds were tested for potential use in forming a solid dechlorination product during thermal dechlorination. The calcium compounds corresponded to calcium oxide (CaO), calcium carbonate ($CaCO_3$), and calcium hydroxide ($Ca(OH)_2$). Such calcium compounds can potentially form $CaCl_2$ as a solid dechlorination product.

To investigate potential formation of solid dechlorination products, a series of samples were heated in a thermogravimetric analysis unit. A sample of polyvinyl chloride (PVC) was heated alone at 250° C. to demonstrate the weight loss due to evolution of HCl during thermal dechlorination. Samples of the calcium compounds alone were also heated to 250° C. to demonstrate that the neat calcium compounds did not undergo mass loss. Finally, a series of 50/50 by weight mixtures were prepared of PVC and each of the calcium compounds. The mixtures were heated to 250° C. to compare the mass loss profile over time.

Thermogravimetric analysis can be used to characterize a thermal process by measuring the amount of weight loss that occurs. The identity of the products is not directly measured. However, in situations where the potential reaction products are well known, thermogravimetric analysis can be used to compare an expected or stoichiometric weight loss with the actual weight loss. For example, the weight of HCl corresponds to roughly 58 wt % of the weight of a polymer repeat unit in PVC. Thus, if all chlorine in a PVC sample was converted to HCl during thermal dechlorination (i.e., stoichiometric conversion), a mass loss of roughly 58 wt % would be expected. As a comparison, the thermal dechlorination of PVC at 250° C. resulted in a measured weight loss of roughly 50 wt % after 4 hours.

Figure 4:
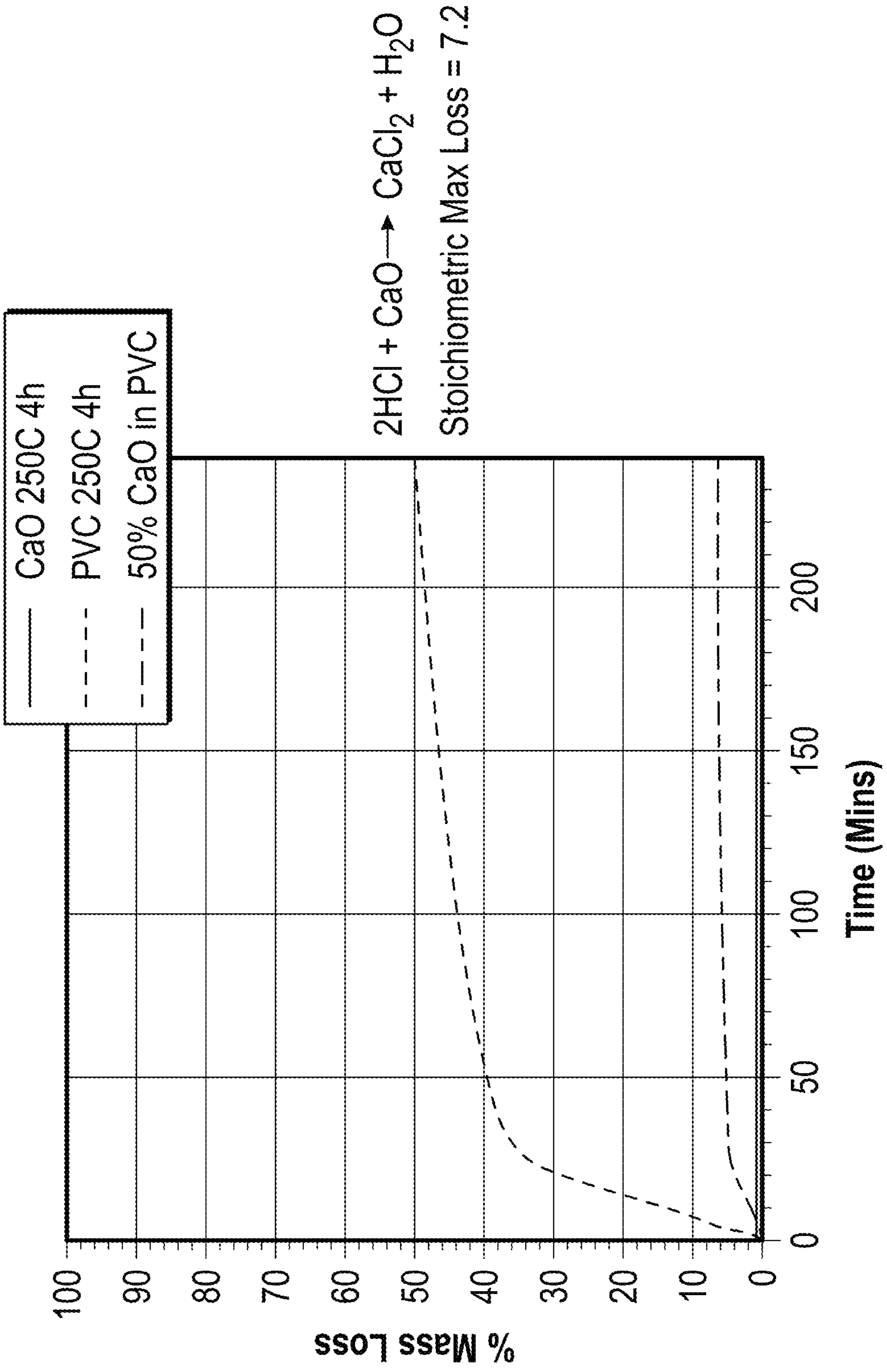
FIG. 4 shows thermogravimetric analysis results a combination of PVC and CaO.

FIG. 4 shows the mass loss profile for the mixture of PVC and CaO. The thermal mass loss curves for PVC and CaO alone are also shown. The expected stoichiometry for the reaction is $2HCl+CaO \Rightarrow CaCl_2+H_2O$. It is noted that water (a relatively low molecular weight compound) is the only gas phase product if chlorine is fully converted to a solid dechlorination product via this reaction. Based on this reaction, if all chlorine in the PVC sample is released under the thermal dechlorination conditions and then converted to $CaCl_2$, the resulting net weight loss would be 7.2 wt %. As shown in FIG. 4, the measured weight loss during the thermogravimetric analysis was between 6.0 wt %-7.0 wt %. It is noted that the difference between the stoichiometric weight loss for the 50/50 PVC plus CaO run and the stoichiometric maximum is proportional to the difference between the weight loss for PVC alone relative to the stoichiometric maximum weight loss if all chlorine were removed from the PVC during a dechlorination process as HCl. This indicates that addition of the CaO was effective for converting chlorine evolved during the thermal dechlorination process into a solid dechlorination product.

Figure 5:
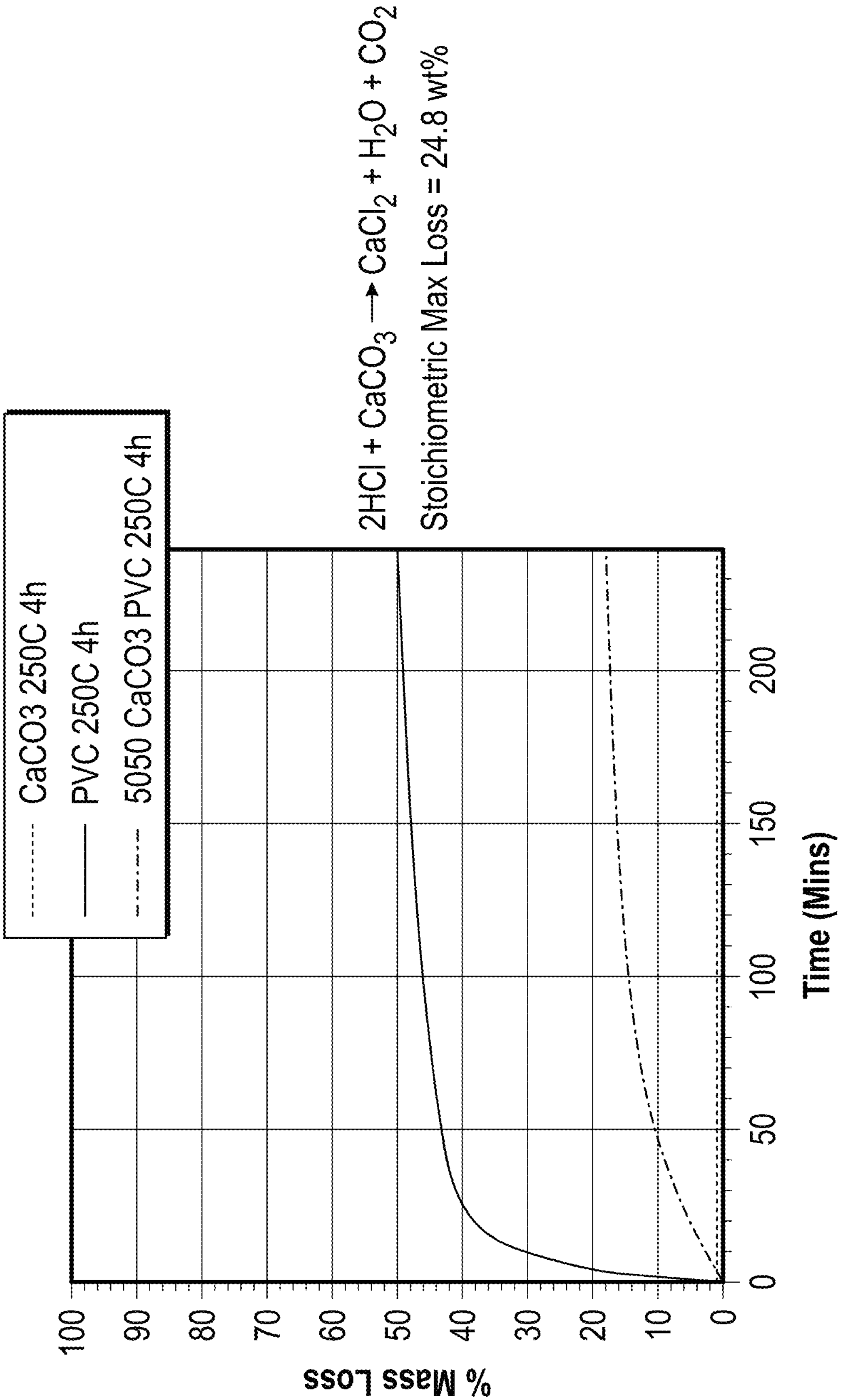
FIG. 5 shows thermogravimetric analysis results a combination of PVC and $CaCO_3$.
Figure 6:
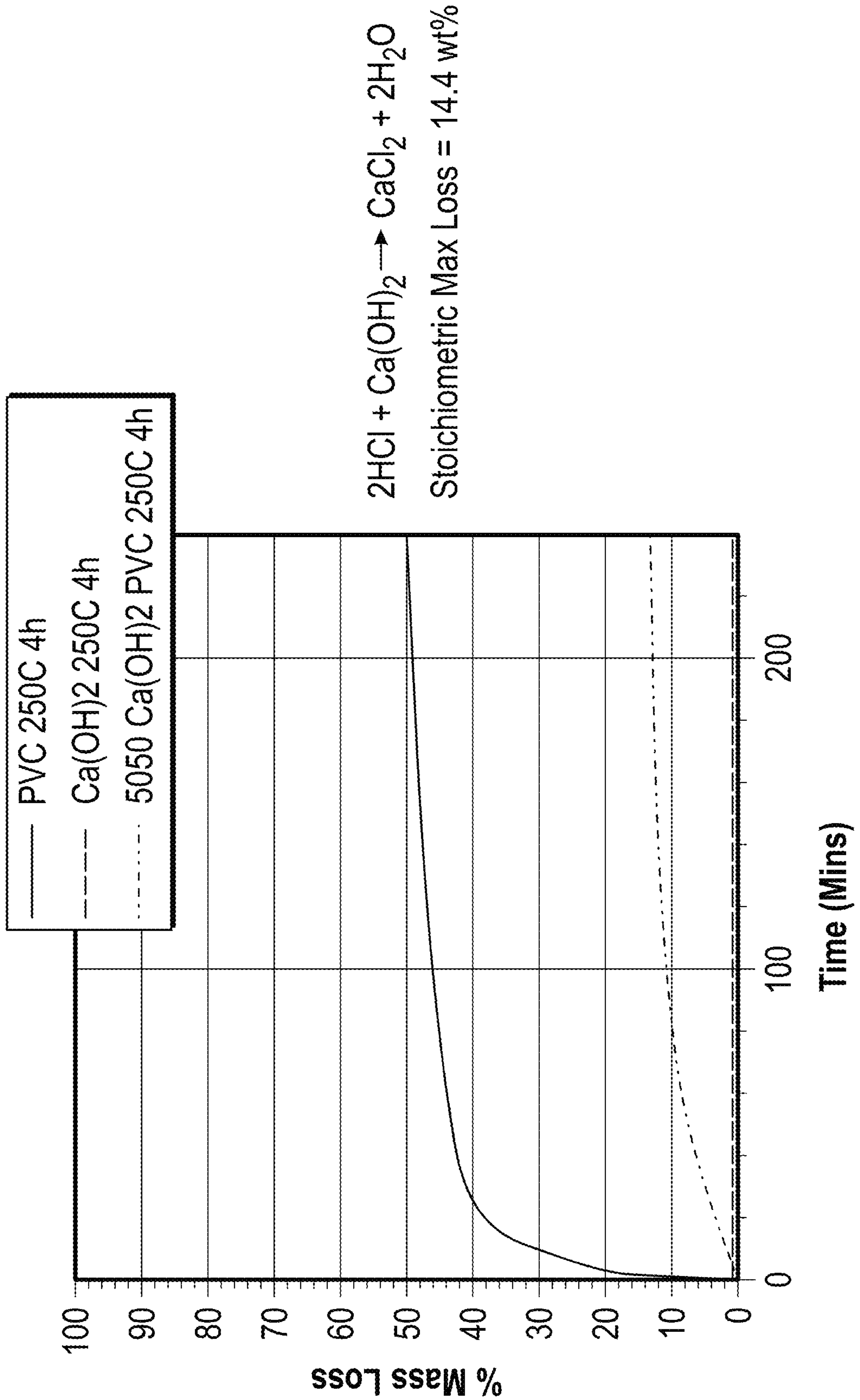
FIG. 6 shows thermogravimetric analysis results a combination of PVC and $Ca(OH)_2$.

FIG. 5 and FIG. 6 similarly show thermogravimetric analysis plots for heating of a 50/50 mixture of PVC with either $CaCO_3$ (FIG. 5) or $Ca(OH)_2$ (FIG. 6). Use of $CaCO_3$ to convert chlorine into a solid dechlorination product would result in a maximum weight loss of roughly 24.8 wt % if all chlorine in the PVC were stoichiometrically converted and resulted in corresponding evolution of both one $H_2O$ and one $CO_2$ for each $CaCl_2$ that is formed. For $Ca(OH)_2$, stoichiometric conversion of chlorine into a solid dechlorination product results in formation of two $H_2O$ molecules per $CaCl_2$, rather than one $H_2O$ and one $CO_2$. As a result, for the plot shown in FIG. 6, the stoichiometric maximum weight loss would roughly 14.4 wt %. As shown in FIG. 5 and FIG. 6, the difference between the expected maximum weight loss and the measured weight loss for the 50/50 mixtures is proportional to the difference in theoretical and measured weight loss values for PVC alone at the thermal dechlorination temperature. Thus, the various calcium compounds appear to be effective at converting substantially all of the evolved chlorine into solid dechlorination products.

Additional Embodiments

Embodiment 1. A method for performing chemical recycling of plastic waste, comprising: thermally dehalogenating a plastic feedstock to form a thermally halogenated feedstock and dehalogenation product; pyrolyzing at least a portion of the thermally dehalogenated feedstock in a pyrolysis reactor at a temperature of 400° C. or more to form a pyrolysis effluent; separating the pyrolysis effluent to form a pyrolysis gas fraction and a pyrolysis liquid fraction; converting at least a portion of the pyrolysis liquid fraction to form a conversion effluent comprising 10 wppm or more of one or more halide components; washing at least a portion of the conversion effluent to remove at least a portion of the one or more halide components from a washed conversion effluent; separating at least a portion of the washed conversion effluent to form a) an ethylene product stream comprising 99.0 vol % ethylene and 1.0 wppm or less of the one or more halide compounds, b) a propylene product stream comprising 99.0 vol % propylene and 1.0 wppm or less of the one or more halide compounds, or c) a combination of a) and b).

Embodiment 2. The method of Embodiment 1, wherein the plastic feedstock comprises 1.0 wt % or more of halogenated polymers.

Embodiment 3. The method of any of the above embodiments, wherein the at least a portion of the pyrolysis liquid fraction comprises a halide content of 100 wppm or less.

Embodiment 4. The method of any of the above embodiments, wherein converting at least a portion of the pyrolysis liquid fraction comprises converting an input flow comprising the at least a portion of the pyrolysis liquid fraction and at least one co-feed, the input flow comprising a halide content of 25 wppm or less.

Embodiment 5. The method of any of the above embodiments, wherein the dehalogenation product comprises HCl, HBr, HI, HF, or a combination thereof.

Embodiment 6. The method of claim any of the above embodiments, wherein pyrolyzing at least a portion of the thermally dehalogenated feedstock comprises pyrolyzing in a fluidized bed of heat transfer particles.

Embodiment 7. The method of any of the above embodiments, i) wherein the heat transfer particles comprise calcium-containing particles; ii) wherein the fluidized bed further comprises calcium-containing particles; iii) wherein the plastic feedstock is thermally dehalogenated in the presence of calcium-containing particles; iv) wherein the dechlorination product comprises $CaCl_2$; v) a combination of two or more thereof; or vi) a combination of three or more thereof.

Embodiment 8. The method of any of the above embodiments, wherein converting at least a portion of the pyrolysis liquid fraction comprises exposing the at least a portion of the pyrolysis liquid fraction to steam cracking conditions, the method optionally further comprising exposing a co-feed to the steam cracking conditions.

Embodiment 9. The method of any of the above embodiments, wherein the pyrolyzing at least a portion of the thermally dehalogenated feedstock further comprises pyrolyzing a recycle portion of the liquid fraction.

Embodiment 10. The method of any of the above embodiments, wherein washing at least a portion of the conversion effluent comprises washing the at least a portion of the conversion effluent in a water wash, an aqueous amine wash, a caustic wash or a combination thereof.

Embodiment 11. The method of any of the above embodiments, further comprising I) washing at least a portion of the pyrolysis gas phase fraction to form a washed pyrolysis gas fraction; II) exposing at least a portion of the pyrolysis gas fraction to an adsorbent bed to form a reduced halogen content pyrolysis gas fraction, or III) a combination thereof.

Embodiment 12. The method of Embodiment 11, wherein converting at least a portion of the pyrolysis liquid fraction further comprises converting at least a portion of the washed pyrolysis gas fraction, converting at least a portion of the reduced halogen content pyrolysis gas fraction, or a combination thereof.

Embodiment 13. The method of Embodiment 11 or 12, wherein separating at least a portion of the washed conversion effluent further comprises separating at least a portion of the washed pyrolysis gas fraction, separating at least a portion of the reduced halogen content pyrolysis gas fraction, or a combination thereof.

Embodiment 14. The method of any of the above embodiments, further comprising oligomerizing, polymerizing, or a combination thereof, at least one of the ethylene product stream and the propylene product stream, wherein the oligomerizing, polymerizing, or a combination thereof, is optionally performed in the presence of a metallocene catalyst, a Ziegler-Natta catalyst, or a combination thereof.

Embodiment 15. The method of any of the above embodiments, wherein separating at least a portion of the washed conversion effluent further comprises forming at least one of a propane-containing product, a butane-containing product, and a butadiene-containing product, and wherein converting at least a portion of the pyrolysis liquid fraction further comprises converting at least a portion of the at least one of a propane-containing product, a butane-containing product, and a butadiene-containing product.

Additional Embodiment A. The method of any of the above embodiments, wherein the plastic feedstock comprises a solution of plastic feedstock in at least one of a recycle stream and a co-feed, and wherein the thermal dehalogenation comprises heating the solution to a temperature of 170° C. to 350° C. in the presence of a purge gas.

Additional Embodiment B. The method of any of the above embodiments, further comprising A) performing contaminant removal on the at least a portion of the thermally dehalogenated feedstock, B) performing contaminant removal on the at least a portion of the pyrolysis liquid fraction, C) performing contaminant removal on at least a portion of the pyrolysis gas fraction, or D) a combination of two or more of A), B), and C).

Additional Embodiment C. The method of any of the above embodiments, wherein the method further comprises washing the plastic feedstock prior to thermally dehalogenating the plastic feedstock.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A method for performing chemical recycling of plastic waste, comprising:

thermally dehalogenating a plastic feedstock to form a thermally dehalogenated feedstock and a dehalogenation product;

pyrolyzing at least a portion of the thermally dehalogenated feedstock in a pyrolysis reactor at a temperature of 400° C. or more to form a pyrolysis effluent;

separating the pyrolysis effluent to form a pyrolysis gas fraction and a pyrolysis liquid fraction;

converting at least a portion of the pyrolysis liquid fraction to form a conversion effluent comprising 10 wppm or more of one or more halide components;

removing contaminant comprising metals from the conversion effluent;

washing at least a portion of the conversion effluent to remove at least a portion of the one or more halide components from a washed conversion effluent;

separating at least a portion of the washed conversion effluent to form a) an ethylene product stream comprising 99.0 vol % ethylene and 1.0 wppm or less of the one or more halide compounds, b) a propylene product stream comprising 99.0 vol % propylene and 1.0 wppm or less of the one or more halide compounds, or c) a combination of a) and b).

2. The method of claim 1, wherein the plastic feedstock comprises 1.0 wt % or more of halogenated polymers.

3. The method of claim 1, wherein the at least a portion of the pyrolysis liquid fraction comprises a halide content of 100 wppm or less.

4. The method of claim 1, wherein converting at least a portion of the pyrolysis liquid fraction comprises converting an input flow comprising the at least a portion of the pyrolysis liquid fraction and at least one co-feed, the input flow comprising a halide content of 25 wppm or less.

5. The method of claim 1, wherein the dehalogenation product comprises HCl.

6. The method of claim 5, wherein the dehalogenation product further comprises at least one of HBr, HF, and HI.

7. The method of claim 1, wherein pyrolyzing at least a portion of the thermally dehalogenated feedstock comprises pyrolyzing in a fluidized bed of heat transfer particles.

8. The method of claim 7, wherein the heat transfer particles comprise calcium-containing particles, or wherein the fluidized bed further comprises calcium-containing particles, or a combination thereof.

9. The method of claim 7, wherein the plastic feedstock is thermally dehalogenated in the presence of calcium-containing particles, or wherein the dechlorination product comprises $CaCl_2$), or a combination thereof.

10. The method of claim 1, wherein converting at least a portion of the pyrolysis liquid fraction comprises exposing the at least a portion of the pyrolysis liquid fraction to steam cracking conditions.

11. The method of claim 10, wherein exposing the at least a portion of the pyrolysis liquid fraction to steam cracking conditions further comprises exposing a co-feed to the steam cracking conditions.

12. The method of claim 1, wherein the pyrolyzing at least a portion of the thermally dehalogenated feedstock further comprises pyrolyzing a recycle portion of the liquid fraction.

13. The method of claim 1, wherein washing at least a portion of the conversion effluent comprises washing the at least a portion of the conversion effluent in a water wash, an aqueous amine wash, a caustic wash or a combination thereof.

14. The method of claim 1, further comprising I) washing at least a portion of the pyrolysis gas phase fraction to form a washed pyrolysis gas fraction; II) exposing at least a portion of the pyrolysis gas fraction to an adsorbent bed to form a reduced halogen content pyrolysis gas fraction, or III) a combination thereof.

15. The method of claim 14, wherein converting at least a portion of the pyrolysis liquid fraction further comprises converting at least a portion of the washed pyrolysis gas fraction, converting at least a portion of the reduced halogen content pyrolysis gas fraction, or a combination thereof.

16. The method of claim 14, wherein separating at least a portion of the washed conversion effluent further comprises separating at least a portion of the washed pyrolysis gas fraction, separating at least a portion of the reduced halogen content pyrolysis gas fraction, or a combination thereof.

17. The method of claim 1, further comprising oligomerizing, polymerizing, or a combination thereof, at least one of the ethylene product stream and the propylene product stream.

18. The method of claim 17, wherein the oligomerizing, polymerizing, or a combination thereof, is performed in the presence of a metallocene catalyst, a Ziegler-Natta catalyst, or a combination thereof.

19. The method of claim 1, wherein the plastic feedstock comprises a solution of plastic feedstock in at least one of a recycle stream and a co-feed, and wherein the thermal dehalogenation comprises heating the solution to a temperature of 170° C. to 250° C. in the presence of a purge gas.

20. The method of claim 1, further comprising A) performing contaminant removal on the at least a portion of the thermally dehalogenated feedstock, B) performing contaminant removal on the at least a portion of the pyrolysis liquid fraction, C) performing contaminant removal on at least a portion of the pyrolysis gas fraction, or D) a combination of two or more of A), B), and C).

21. The method of claim 1, wherein the method further comprises washing the plastic feedstock prior to thermally dehalogenating the plastic feedstock.

22. The method of claim 1, wherein separating at least a portion of the washed conversion effluent further comprises forming at least one of a propane-containing product, a butane-containing product, and a butadiene-containing product, and wherein converting at least a portion of the pyrolysis liquid fraction further comprises converting at least a portion of the at least one of a propane-containing product, a butane-containing product, and a butadiene-containing product.

* * * * *